(12) United States Patent
Tepe et al.

(10) Patent No.: US 7,423,132 B2
(45) Date of Patent: Sep. 9, 2008

(54) METHOD FOR THE ENRICHMENT AND CHARACTERIZATION OF PHOSPHORYLATED PEPTIDES OR PROTEINS

(75) Inventors: Jetze J. Tepe, East Lansing, MI (US); Thomas J. Pinnavaia, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 86 days.

(21) Appl. No.: 11/147,073

(22) Filed: Jun. 7, 2005

(65) Prior Publication Data

US 2006/0014234 A1    Jan. 19, 2006

Related U.S. Application Data

(60) Provisional application No. 60/579,246, filed on Jun. 14, 2004.

(51) Int. Cl.
*C07K 1/14* (2006.01)

(52) U.S. Cl. ................. 530/412; 530/352; 530/402; 530/415; 530/427

(58) Field of Classification Search ............... 530/352, 530/402, 412, 415, 427
See application file for complete search history.

(56) References Cited

OTHER PUBLICATIONS

Miklos, G.L.G., et al., Proteomics 1 30-41 (2001).
Manning, G., et al., Science 298 1912-1934 (2002).
Kaufmann, H., et al., Proteomics 1, 194-199 (2001).
Sherr, C.J., Science 274 1672-1677 (1996).
Klumpp, S., et al., Curr Opin Pharmacol 2 458-462 (2002).
Desbois-Mouthon, C., et al., Metabolism 45 1493-1500 (1996).
Saltiel, A.R., Am J Physiol 270 E375-385 (1996).
Hanger, D.P., et al., J. Neurochem 71 2465-2476 (1998).
Senior, K., Drug Discov Today 5 311-313 (2000).
Cohen, P., Eur J Biochem 268 5001-5010 (2001).
Borman, S., Chemistry and Engineering News Nov. 26, 27-29 (2001).
Fields, S., Science 291 1221-1224 (2001).
Burbaum, J., et al., Curr OpinChem Biol 6 427-433 (2002).
Cohen, P., Nat Rev Drug Discov 1 309-315 (2002).
Damer, C.K., et al., J Biol Chem 273 24396-24405 (1998).
McLachlin, D.T., et al., Current Opinion in Chemical Biology 5, 591-602 (2001).
Knight, Z.A., et al., Nat. Biotechnol. 21 1047-1054 (2003).
Zhou, H., et al., Nat Biotechnol 19 375-378 (2001).
Oda, Y., et al., Nat Biotechnol 19 379-382 (2001).
Thaler, F., et al., Anal. Bioanal. Chem. 376 366-373 (2003).
Bridges, A.J., Chem Rev 101 2541-2572 (2001).
Lisacek, F.C., et al., Proteomics 1 186-193 (2001).
Minakuchi, H., et al., Anal. Chem. 68 3498-3501 (1996).
Cabrera, K., et al., J High Resol Chromatog23 93-99 (2000).
Timpermann, A.T., et al., Anal Chem 72 4115-4121 (2000).
Butt, A., et al., Proteomics 1 42-53 (2001).
Westbrook, J.A., et al., Proteomics 1 370-376 (2001).
Posewitz, M.C., et al., Anal Chem 71 2883-2892 (1999).
Figeys, D., et al., Anal Chem 71 2279-2287 (1999).
Ficcarro, S.B., et al., Nat Biotechnol20 301-305 (2002).
D.E. Bergbreiter,Medicinal Research Reviews 1999, 19(5), 439-450.
A. Stein, Adv. Mater. 2000, 12(19), 1403-1419.
S. Hamoudi, Chem. Mater. 2001, 13(10), 3151-3168.
F. Schueth, Chem. Mater. 2001, 13(10), 3184-3195.
El Haskouri et al., European J. Inorg. Chem., 2004 (9), 1804-1807.
M.C. Burleigh et al., Colloid Polym. Sci. 2004, 282(7), 728-733).
A. Clearfield, Z. Wang, J Chem. Soc., Dalton Transactions2002, (15), 2937-2947.
A. I. Khan, I.

*Primary Examiner*—David Lukton
(74) *Attorney, Agent, or Firm*—Ian C. McLeod

(57) ABSTRACT

A method for the separation and assay of phosphorylated peptides or proteins from complex mixtures of proteins and peptides is described. The method uses a diazo moiety linked by an organic group to a substrate. Kits for performing the assay are also described. The method and kits are particularly useful for detecting changes in phosphorylates produced in living cells.

44 Claims, 3 Drawing Sheets

MALDI-*tof* mass spectrum of the methylated glycogen phosphorylase A digestion products of Example 3.

MALDI-*tof* mass spectrum of the phosphorylated fragmentation products separated from the digest by the method of Example 3.

METHOD FOR THE ENRICHMENT AND CHARACTERIZATION OF PHOSPHORYLATED PEPTIDES OR PROTEINS

CROSS REFERENCE TO RELATED APPLICATION

This application claims priority to Provisional application Ser. No. 60/579,246, filed Jun. 14, 2004.

STATEMENT REGARDING FEDERALLY SPONSORED RESEARCH OR DEVELOPMENT

Not Applicable

STATEMENT REGARDING GOVERNMENT RIGHTS

Not Applicable

BACKGROUND OF THE INVENTION (1) Field of the Invention

The present invention relates to a process for the enrichment and characterization of phosphorylated proteins and peptides from complex mixtures. In particular, the present invention relates to a multi-step procedure, suitable for implementation in kit form, wherein appropriately protected phosphorylated proteins or peptides are captured by reaction with a diazo moiety linked to a separation medium, isolated from the non-phosphorylated components of the mixture, released from the separation medium, and subsequently characterized by physicochemical means.

(2) Description of Related Art

The reversible process of phosphorylation/dephosphorylation of proteins is a post-translational protein modification that is crucial for intercellular signal transduction. Protein phosphorylations are widely recognized as critical events in the regulation of division, gene expression and metabolism (Venter, J. C., et al., *Science* 291 1304-1351 (2001); Miklos, G. L. G., et al., *Proteomics* 1 30-41 (2001); Patarca, R., *Crit. Rev. Oncog.* 7 343-432 (1996); and Manning, G., et al., *Science* 298 1912-1934 (2002)). It is estimated that more than one third of all proteins can be modified by phosphorylation in mammalian cells and up to 2% of the genes in a vertebrate genome encode either protein kinases or phosphatases (Manning, G., et al., *Science* 298 1912-1934 (2002); and Kaufmann, H., et al., *Proteomics* 1, 194-199 (2001)). Deregulation of the signal transduction cascade upsets this well-balanced system and has been implicated in diseases such as cancer, (Sherr, C. J., *Science* 274 1672-1677 (1996); Klumpp, S., et al., *Curr Opin Pharmacol* 2 458-462 (2002)) type II diabetes (Desbois-Mouthon, C., et al., *metabolism* 45 1493-1500 (1996); Saltiel, A. R., *Am J Physiol* 270 E375-385 (1996)), cystic fibrosis (Gadsby, D. C., et al., *Physiol Rev* 79 S77-S107 (1999)), Alzheimer's disease (Goedert, M., et al., *Biochem Soc Trans* 23 80-85 (1995); Hanger, D. P., et al., *J. Neurochem* 71 2465-2476 (1998); Senior, K., *Drug Discov Today* 5 311-313 (2000)); Liu, D. X., et al., *Cell Tissue Res* 305 217-228 (2001)) and many more (Cohen, P., *Eur J Biochem* 268 5001-5010 (2001)).

Even though the human genome map presents invaluable insight into the structure and sequence of our genes, it offers limited insight into these critical post-translational protein modifications. Unfortunately, proteomic techniques relevant to the elucidation of signal transduction have been lacking in development in comparison to genomic technologies (Borman, S., *Chemistry and Engineering News* November 26, 27-29 (2001); Fields, S., *Science* 291 1221-1224 (2001); Burbaum, J., et al., *Curr Opin Chem Biol* 6 427-433 (2002)). In light of the role of protein phosphorylations in cellular deregulation, a universal phospho-enrichment technique would be of great value to improved strategies for drug design and target validation (Cohen, P., *Eur J Biochem* 268 5001-5010 (2001); and Cohen, P., *Nat Rev Drug Discov* 1 309-315 (2002)).

Proteomic research is focused the identification of the phosphorylation states of proteins and of the specific phosphorylation site of proteins. The first step in the mapping of the phosphorylation sites in proteins generally requires the digestion of phosphoproteins or protein complexes into an intricate mixture of its corresponding smaller peptide fragments. Despite several recent advances in tandem mass spectrometry and Edman degradation, the characterization of a complex pool of phosphorylated and non-phosphorylated peptides is still a very tedious or sometimes impossible task (Damer, C. K., et al., *J Biol Chem* 273 24396-24405 (1998); MacDonald, J. A., et al., *Mol. Cell. Proteomics* 1 314-322 (2002)). The most common technique currently used to enrich the phosphorylated substrates from the peptide pool is by the use of immobilized metal affinity chromatography (IMAC) (Andersson L., et al., *Analytical Biochemistry* 154 250-254 (1986)). Due to the non-covalent binding of the substrate to the column, loss of phosphopeptides, difficulties in eluding multiple phosphorylated peptides and high background from non-phosphorylated peptides has limited this approach (McLachlin, D. T., et al., *Current Opinion in Chemical Biology* 5, 591-602 (2001)). Recently, intense research has been focuses on the chemical identification of phosphorylation sites. Despite the power of this approach, current methods are still limited to the identification of serine and threonine residues (Knight, Z. A., et al., *Nat. Biotechnol.* 21 1047-1054 (2003); Zhou, H., et al., *Nat Biotechnol* 19 375-378 (2001); Oda, Y., et al., *Nat Biotechnol* 19 379-382 (2001); Thaler, F., et al., *Anal. Bioanal. Chem.* 376 366-373 (2003)).

It has been stated, "The work that has been done with genome sequencing (in the Human Genome Project) may turn out to have been trivial by comparison with the challenge we now face trying to understand proteins"—Francis S. Collins, director of the National Human Genome Research Institute, in "*Any New Proteomic Techniques Out There?*" (Borman, S., *Chemistry and Engineering News* November 26, 27-29 (2001)). In an effort to tackle the lack of proteomic techniques, the Human Proteome Organization (HUPO) has been established to consolidate national and regional proteome organizations in a worldwide organization to encourage the spread of proteomic technologies. The main obstacle in proteomic analysis is the lack of techniques to identify post-translational protein modifications, such as protein phosphorylations, glycosylation, and acylations. Protein phosphorylations are widely recognized as crucial events in intercellular signal transduction and regulation of numerous cellular events such as growth, division, gene expression and metabolism (Miklos, G. L. G., et al., *Proteomics* 1 30-41 (2001); Patarca, R., *Crit. Rev. Oncog.* 7, 343-432 (1996)). Deregulation of the signal transduction cascade upsets this well-balanced system and has been implicated in diseases such as cancer (Sherr, C. J., *Science* 274 1672-1677 (1996); and Klumpp, S., et al., *Curr Opin Pharmacol* 2 458-462 (2002)), type II diabetes (Desbois-Mouthon, C., et al., *metabolism* 45 1493-1500 (1996); Saltiel, A. R., *Am J Physiol* 270 E375-385 (1996)), cystic fibrosis (Gadsby, D. C., et al., Physiol Rev 79 S77-S107 (1999)), Alzheimer's disease (Goedert, M., et al., *Biochem Soc Trans* 23 80-85 (1995); Hanger, D. P. et al., *J Neurochem* 71 2465-2476 (1998); and Liu, D. X., *Cell Tissue Res* 305 217-228 (2001)) and many more (Cohen, P., *Eur J Biochem* 268 5001-5010 (2001)). Many age related neurological disorders such as Alzheimer's are caused by neuronal apoptosis. Upregulation of cyclin D-CDK4/6 and the deregulation of the E2F transcription are the key events in the early stages of these diseases (Liu, D. X., et al., *Cell Tissue Res* 305 217-228 (2001)). Deregulation of cyclin dependent kinases such a GSK-3β have been associated in abnormal phosphorylation of the microtubulin-binding Tau, which are also diagnostic for Alzheimer's disease (Imahori, K., et al., *J Biochem* (Tokyo) 121 179-188 (1997); Augustinack, J. C., et al., *Acta Neuropathol* (Berl) 103 26-35 (2002); Imahor, K., et al., *Neurobiol Aging* 19 S93-S98 (1998)). Other diseases such as cancer are directly related to the deregulation of protein phosphorylations. More than 80% of adult cancers in the US are age related carcinomas, which emphasizes the importance of cumulative exposures to environmental carcinogens that affect these critical signal transduction cascades (Sherr, C. J., *Science* 274 1672-1677 (1996)). Deregulation of the proteins that govern the positive and negative regulatory phosphorylation of the cell cyclic pathways (for example, the cyclin dependent kinases, CDK's) are frequently found in head and neck carcinomas, esophageal carcinomas, bladder cancer, primary breast carcinoma, small-cell lung tumors and hepatocellular carcinomas and others (Sherr, C. J., *Science* 274 1672-1677 (1996); and Hall, M., et al., *Adv. Cancer Res* 68 67-108 (1996)).

The systematic identification of deregulations in protein phosphorylation would therefore provide unprecedented insight in the potential cause and treatment of these diseases. Currently, there are less then 200 molecular targets for all therapeutic agents on the market, half of which are G-protein-coupled receptors (Bridges, A. J., *Chem Rev* 101 2541-2572 (2001)). This very limited selection of targets is a direct consequence of the lack of efficient proteomic techniques used to identify novel targets in these protein deregulations. Even though the decoding of the human genome has provided some new potential targets, insight into post-translational protein modifications, such as protein phosphorylations, are the key to the elucidation of drug mechanisms, cell signaling and target validation (Burbaum, J., et al., *Curr Opin Chem Biol* 6 427-433 (2002)). It would therefore not only be of great medicinal and diagnostic value to identify the point of origin of cellular deregulation in these diseased cells, but this information would also provide many potential targets for pharmaceutical agents.

There is little doubt that proteomic techniques relevant to the elucidation of signal transduction have been lacking in development in comparison to genomic technologies (Borman, S., *Chemistry and Engineering News* November 26, 27-29 (2001); and Fields, S., *Science* 291 1221-1224 (2001)) and that to date there are no efficient and universal techniques available for the characterization of phosphorylation signal transduction cascades in cells. Phosphoproteomic research is focused the identification of the phosphorylation states of proteins and of the specific phosphorylation site of proteins. The first step in the mapping of the phosphorylation sites in proteins generally requires the digestion of phosphoproteins or protein complexes into an intricate mixture of its corresponding smaller peptide fragments. Despite several recent advances in tandem mass spectrometry and Edman degradation, the characterization of a complex pool of non-phosphorylation containing a few phosphorylated peptides generally becomes a very tedious or sometimes impossible task (Damer, C. K., et al., *J Biol Chem* 273 24396-24405 (1998); and MacDonald, J. A., et al., *Mol. Cell. Proteomics* 1 314-322 (2002)). The most common technique currently used to enrich the phosphorylated substrates from a peptide pool is by the use of immobilized metal affinity chromatography (IMAC) (Andersson, L., et al., *Analytical Biochemistry* 154 250-254 (1986)). The isolated peptides are subsequently sorted and matched against the GenBank using available data programs (Damer, C. K., et al., *J Biol Chem* 273 24396-24405 (1998); and Lisacek, F. C., et al., *Proteomics* 1 186-193 (2001)). Because IMAC is based on anion-specific affinity binding mechanism for linking the substrate to the column, loss of phosphopeptides, difficulties in eluding multiple phosphorylated peptides and high background from non-phosphorylated peptides has limited this approach (McLachlin, D. T., et al., *Current Opinion in Chemical Biology* 5 591-602 (2001)). Moreover, additional new methods are limited to the identification of serine and threonine residues (Knight, Z. A., et al., *Nat. Biotechnol.* 21 1047-1054 (2003); Thaler, F., et al., *Anal. Bioanal. Chem.* 376 366-373 (2003); Zhou, H., et al., *Nat Biotechnol* 19 375-378 (2001); and Oda, Y., et al., *Nat Biotechnol* 19 379-382 (2001)). A short description of some of some of the most common techniques is listed below:

Protein analysis is traditionally accomplished through 2D electrophoresis to separate the proteins, followed by the detection of the native or digested proteins using Edman degradation or mass spectrometric (MS) methods. In order to concentrate and separate proteins by more efficient high performance liquid chromatography (HPLC) and related adsorption methods, it is necessary to carefully control surface polarity and chemical function of the adsorbent, as well as the pore size, surface area, pore volume of the adsorbent. The current commercial state of the art in chromatography and affinity binding for the separation of peptides/proteins is based on the use of functionalized resins and metal oxides, particularly silica. The commercial resins and oxides in current use achieve separations through various physical processes, including electrostatic, complexation and reverse phase (hydrophobic) binding processes. In the case of HPLC, one also needs to control the particle size and texture of the adsorbent to avoid unworkable back-pressures. For instance, an efficient number of theoretical plates can be achieved with silica particles of 3.5 micrometer in diameter, but the flow rate is limited to a maximum of only 4 mL/min at a maximum operational back-pressure of 300 barr. Important improvements in flow rates at the same theoretical plate heights afforded by 3.5 micrometer particles have been made recently through the use of monolithic silica columns with flow-through macropores and diffusional mesopores (Nakanishi, K., et al., *J. Non-Crystal. Solids* 139 1-13 (1992); Minakuchi, H., et al., *Anal. Chem.* 68 3498-3501 (1996)). Merck, KGaA now markets these columns under the trade name Chromolith (Cabrera, K., et al., *J High Resol Chromatog* 23 93-99 (2000); Lubda, D., et al., $2^{nd}$ *International Conference on Silica*, Mulhouse, France September 3-6 (2001)). Also, Millipore Corporation has developed functional resin-based supports that greatly simplify the concentration of certain classes of peptides/proteins through affinity binding and related methodologies (For example see the Milipore, I. w.a.w.m.c.). Despite these important advances in proteomics, still greater specificity is needed in identifying post-translational protein modification, which ultimately regulates all cellular events.

Traditional techniques in phosphoprotein characterization involve $^{32}P$ labeling of isolated proteins followed by digestion and HPLC purification or two-dimensional electrophoresis (Timperman, A. T., et al., *Anal Chem* 72 4115-4121 (2000); Butt, A., et al., *Proteomics* 1 42-53 (2001); Westbrook, J. A., et al., *Proteomics* 1 370-376 (2001)). The isolated radiolabeled phosphorylated peptides are subsequently characterized by Edman degradation or mass spectrometry. Alternatively, antibody precipitation (Kaufmann, H., et al., *Proteomics* 1 194-199 (2001)), biotinylation of modified phosphoserine residues via a beta-elimination of the phosphate group (Zhou, H., et al., *Nat Biotechnol* 19 375-378 (2001)) or even multistep (six step) procedures for the chemical modification of phosphopeptides (Oda, Y., et al., *Nat Biotechnol* 19 379-382 (2001)) have been used to isolate specific phosphorylated substrates. Recently, intense research has been focused on the chemical identification of phosphorylation sites. Despite the power of this approach, current methods are still limited to the identification of serine and threonine residues or require multistep procedures (Knight, Z. A., et al., *Nat Biotechnol* 21 1047-1054 (2003); Thaler, F., et al., *Anal Bioanal Chem* 376 366-373 (2003); Zhou, H., et al., *Nat Biotechnol* 19 375-378 (2001); and Oda, Y., et al., *Nat Biotechnol* 19 379-382 (2001)).

Enrichment of phosphopeptides by immobilized metal affinity chromatography (IMAC) is one of the most common techniques used today. IMAC can be used to preferentially bind to the negatively charged phosphate groups, but they also bind to non-phosphorylated residues such as glutamic and aspartic acid, which also carry a negative charge (Posewitz, M. C., et al., *Anal Chem* 71 2883-2892 (1999)), thus compromising selectivity. In addition, nonselective metal-ligand complexes with histidines also result in the isolation of the non-phosphorylated substrates. Due to the non-covalent binding of the substrate to the column, loss of phosphopeptides, difficulties in eluding multiple phosphorylated peptides and high background from non-phosphorylated peptides has limited this approach (McLachlin, D. T., et al., *Current Opinion in Chemical Biology* 5 591-602 (2001)). Recent advances in proteomic analysis using tandem mass spectrometry (Figeys, D., et al., *Electrophoresis* 19 1811-1818 (1998); Figeys, D., et al., *Anal Chem* 71 2279-2287 (1999)) and Edman degradation has allowed for the identification of phosphorylated peptides by mixed peptide sequencing and database searching (Damer, C. K., et al., *J Biol Chem* 273 24396-24405 (1998); MacDonald, J. A., et al., *Mol Cell Proteomics* 1 314-322 (2002); and Mackey, A. J., et al., *Mol Cell Proteomics* 1 139-147 (2002)). With the increase and reliability of these protein databases, peptide mass fingerprinting is currently the method of choice for the rapid identification of proteins (Lisacek, F. C., et al., *Proteomics* 1 186-193 (2001); and Mackey, A. J., et al., *Mol Cell Proteomics* 1 139-147 (2002)). Unfortunately, these techniques display severe limitations concerning their in vivo analysis of phosphorylated proteins. In addition, the identification and characterization of a single phosphorylation site in a protein digest, composed of a complex mixture of hundreds of peptides, renders a tedious and often an impossible task even with the most advanced proteomic techniques.

The enrichment of phosphorylated proteins using an IMAC™ ion exchange resin is based on the reversible coordination of phosphate groups to metal ion (usually $Fe^{3+}$ or $Ga^{3+}$) binding sites immobilized on the resin. This reversible process of metal-ligand binding results in experimental limitations and drawbacks in peptide selectivity. These limitations include a loss of phosphopeptides and a relatively high background from unphosphorylated peptides with metal binding affinities and difficulties in eluding multiple phosphorylated peptides (McLachlin, D. T., et al., *Current Opinion in Chemical Biology* 5 591-602 (2001)). Even though methylation of the peptide digest decreases the amount of unspecific metal-ligand binding with carboxylic acid residues, it does not exclude the binding of other metal binding residues present such as histidine residues (Ficcarro, S. B., et al., *Nat Biotechnol* 20 301-305 (2002)).

OBJECTS

It is therefore an object of the present invention to provide a method which enables the selection of specific phosphorylated proteins and peptides for the purpose of identification, analysis and disease diagnosis. Further, it is an object of the present invention to provide a method which is reliable and that can be made generally available in the form of kits for use by practitioners of proteomic science and technology. These and other objects will become increasingly apparent by reference to the following description.

SUMMARY OF THE INVENTION

Figure 1:
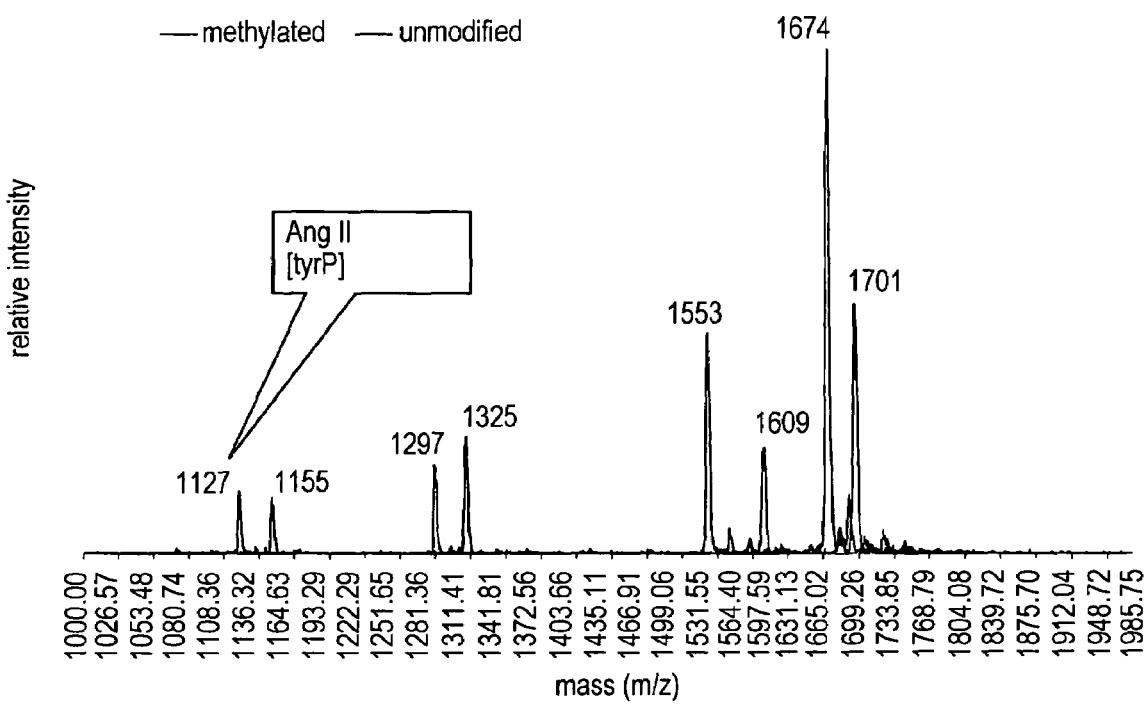
FIGS. 1 and 2 are mass spectra as described in Example 2.

A method for the separation and method for the compositional analysis of phosphorylated proteins or peptides from a protein or peptide mixtures is disclosed herein.

Chapter 4 of the Ph.D. thesis by Jetze Tepe entitled "Selective Isolation Of Phosphorylated Peptides Utilizing Solid Support", University of Virginia 1998, (exhibit A) describes a method for trapping of phosphorylated peptides obtained through the digestion of a purified protein of known composition. A diazo moiety on a linker molecule bound to a resin substrate is displaced by the phosphate group so that the phosphate is bound by the linker molecule. In addition to being limited to the enrichment of peptide fragments from a single protein of known composition, the method did not demonstrate usefulness for the comparative characterization of phosphorylated cell proteins and peptides. There is a need to develop a general method for the characterization of phosphorylated proteins and peptides so that it is applicable to complex and unknown mixtures. There is also a need for a method that allows for the characterization of phosphorylated proteins and peptides derived from immuno-precipitates. The comparative analysis of, the phosphorylated proteins and peptides obtained from immuno-precipitates would allow cells in a healthy and in a diseased state to be distinguished. A comparative analysis of phosphorylated proteins and peptides would also allow for the identification of cells that have been subjected to external factors that influence cell function, such as radiation, toxins, and drugs. Also, there is a need to integrate the multi-step procedures for the characterization of phosphorylated proteins and peptides into a general method that can be provided in the form of a kit for use in protein analysis, for comparisons of protein compositions, for the detection of factors that influence protein signaling pathways within cells, for the differentiation of cells, for the identification of cells that have been exposed to exogenous stimuli and, ultimately, for the diagnosis of diseases. The present invention addresses these needs by providing in part a reliable and efficient methodology through the integration of several procedures that include in part the protection of carboxylate groups which otherwise would interfere with the immobilization of phosphorylated moieties, the diazo functionalization of separation media for the selective immobilization of the phosphorylated moieties, the release of the phosphorylated moieties from the separation media, and the determination of the composition of the released phosphorylated moieties. Most importantly, the integrated methodology is applicable to unknown and complex mixtures of proteins and peptides, including those derived from living cells. Still further, the integrated methodology of this invention allows for the design of kits for facile use by proteomic scientists and practitioners. The methodology of this invention in its preferred embodiment discloses methods for the protection of the carboxylate groups of proteins and peptides through esterification, amination, and thiolation reactions. In the absence of such protection reactions, any protein or peptide moiety containing a carboxylate group could react with the diazo-functionalized separation medium and thereby lower the specificity of the separation medium toward phosphorylated moieties.

More specifically, the present invention relates to a method for the separation of phosphorylated proteins or peptides from a protein or peptide mixture which comprises:

(a) providing protein or peptide mixture of unknown chemical composition comprising the phosphorylated proteins or peptides;

(b) protecting any carboxylate groups in the mixture of step (a) by reaction with an esterification agent or an amination agent or a thiolating agent.

(c) reacting the mixture of step (b) with a diazo group-substituted organic moiety linked to a separation medium to bind a phosphate group of the phosphorylated protein or peptide to the organic moiety in place of the diazo group;

(d) separating the phosphorylated proteins or peptides bound to the separation medium from the mixture; and (e) releasing the bound phosphorylated proteins or peptides from the separation medium.

Further, the present invention relates to a method for the compositional analysis of phosphorylated proteins or phosphorylated peptides from a protein or peptide mixture which comprises:

(a) providing a protein or peptide mixture comprising the phosphorylated proteins or peptides of unknown chemical composition;

(b) protecting any carboxylate groups in the mixture of step (a) by reaction with an esterification agent, an amination agent, thiolating agent or olefins generating structures of the formulas:

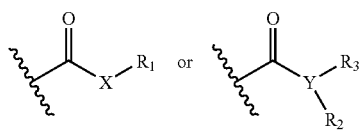

wherein X comprises oxygen or sulfur, Y is nitrogen and R1, R2 and R3 are selected from the group consisting of hydrogen, an alkyl, acyl or aryl moieties and mixtures thereof;

(c) reacting the mixture of step (b) with a diazo group-substituted organic moiety linked to a separation medium to bind a phosphate group of the phosphorylated protein or peptide to the organic moiety in place of the diazo group;

(d) separating the phosphorylated proteins or peptides bound to the separation medium from the mixture;

(e) releasing the bound phosphorylated proteins or peptides from the separation medium; and (f) subjecting the released phosphorylated proteins or peptides in step (e) to chemical and physical analytical analysis to at least in part determine the chemical composition of the phosphorylated entities.

Preferably the mixture of proteins or peptides is from living cells. Preferably the mixture of peptides or proteins is obtained from sources selected from the group consisting of: cell extracts obtained through cell lysis; complexes formed through immuno-precipitation; products formed through the digestion of protein extracts; products formed through the digestion of immuno-precipitates, and mixtures thereof. Preferably the carboxylate groups of the protein or peptide are protected from reaction with the diazo groups of the separation medium by reaction methods selected from the group consisting of:

(a) esterification by an esterifying agent selected from the group consisting of alkyl alcohols, aryl alcohols, alkyl halide, aryl halide, alkyl triflate, aryl triflate, and mixtures thereof;

b) amination by an amidating agent selected from the group consisting of an alkyl amine or aryl amine; and c) esterification by isobutylene catalyzed by a mineral acid.

Preferably the protection of the carboxylate groups of the peptide or protein is carried out in an acidic anhydrous alcohol solution formed by the reaction of an acid chloride or anhydride with alcohols or by protection of the carboxylate groups with isobutylene catalyzed by a mineral acid. Preferably the diazo group used to bind a phosphate group of the phosphorylated protein or peptide to the separation medium in place of the diazo group has the general formula:

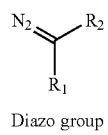

Diazo group and wherein $R_1$ and $R_2$ are selected from the group consisting of hydrogen, a carbonyl group, an ester, an amide, an aryl group, an alkyl group, an acyl group, an aryl group, an arylalkyl group, a heteroaryl group, a homocyclic ring containing 5-14 carbon atom members, a heterocyclic ring containing 4-12 ring members, organo halides, alkoxides, organo sulfoxides, organo sulfonates, organo phosphonates, and combinations thereof.

Preferably the diazo group used to bind a phosphate group of the phosphorylated protein or peptide to the separation medium in place of the diazo group has the general formula:

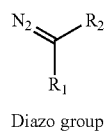

Diazo group and wherein $R_1$ is hydrogen and $R_2$ is a resonance stabilizing organic moiety.

Preferably the diazo group of the separation medium is an α-diazo group prepared by diazotization of an amine functionality. Preferably the diazo group of the separation medium is an α-diazo group prepared by reaction of a diazoalkane with a

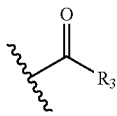

group bound to the separation medium wherein $R_3$ is selected from the group consisting of an amide a halide, an alkoxide, a thiol, an amine, amide, trichloromethyl, trifluoromethyl, acid, succinamide, cyano, azide, sulfonate, phosphite sulfite or derivatives thereof. Preferably the diazo group is linked to the separation medium trough a linker group consisting of aryl groups (Wang-type linkers), polyethylene glycol (PEG), bis 2-acrylamide based PEG co-polymers (PEGA), Rink amides and derivatives and combinations thereof.

Preferably the separation medium is selected from the group consisting of: a resin; a porous resin; a polymer; a thermomorphic polymer; a metal oxide; a metal hydroxide; a mesoporous metal oxide; a mesoporous metal hydroxide; a metal; a layered silicate clay, a layered metal phosphate; a layered metal phosphonate; and combinations thereof. Preferably the separation medium is in thin-film, powdered, bead, gel, foam, sponge, or fibrous form. The separation medium can also be in liquid form.

The bound phosphorylated proteins or peptides are released from the separation medium by a chemical reaction, a thermal reaction, a photochemical reaction, or combinations thereof. The bound phosphorylated proteins or peptides are released from the separation medium through chemical reaction with an acid or a base. The bound phosphorylated proteins or peptides are released from the separation medium by reaction with an acid selected from the group consisting of mineral acids, carboxylic acids, and halogenated carboxylic acids. Preferably the acid is selected from the group consisting of hydrochloric acid, sulfuric acid, phosphoric acid, acetic acid and trifluoroacetic acid. Preferably the bound phosphorylated proteins or peptides are released from the separation medium by reaction with a base selected from the group consisting of sodium hydroxide, ammonium hydroxide, and buffers at a pH value >7. Preferably the bound phosphorylated proteins or peptides are released from the separation medium by physical methods selected from the group consisting of ablation and sublimation. Preferably the bound phosphorylated proteins or peptides are released from the separation medium by photolytical means by treatment of the separation medium with different wavelengths of light. Preferably the bound phosphorylated proteins or peptides are released from the separation medium by enzymatic reaction using enzymes selected from the group comprising esterases, phosphatase, lipases or proteases.

The present invention also relatees to a kit for the separating of phosphorylated proteins or peptides from a protein or peptide mixture which comprises:

(a) providing a diazo group-substituted organic moiety linked to a separation medium; and (b) instructions enabling use of the kit including methods for reacting the mixture with a diazo group-substituted organic moiety linked to a separation medium to bind a phosphate group of the phosphorylated protein or peptide to the organic moiety in place of the diazo group, use of an esterifying reagent to esterify any carboxylic acid groups in the protein or peptide mixture, use of reagents and methods for separating the phosphorylated proteins or peptides bound to the separation medium from the mixture, and use of reagents and methods for releasing the bound phosphorylated proteins or peptides from the separation medium.

The present invention also relates to a kit for the compositional analysis of phosphorylated proteins or peptides from a protein or peptide mixture which comprises:

(a) providing a diazo group-substituted organic moiety linked to a separation medium;

(b) instructions enabling use of the kit, including instructions for reacting the mixture with an diazo group substituted organic moiety linked to a separation medium to bind a phosphate group of the phosphorylated protein or peptide to the organic moiety in place of the diazo group, use of an esterifying reagent to esterify any carboxylic acid groups in the protein or peptide mixture, use of reagents and methods for separating the phosphorylated proteins or peptides bound to the separation medium from the mixture and use of reagents and methods for releasing the bound phosphorylated proteins or peptides from the separation medium, and (c) instructions enabling the determination of the composition of the released phosphorylated proteins or peptides in step (b) by chemical and physical analytical methods. Preferably the instructions provide for the separation and compositional analysis of peptides or proteins from living cells. Preferably the analytical methods of step (c) are selected from the group consisting of Edman degradation, mass spectroscopy, MALDI mass spectroscopy, nuclear magnetic resonance spectroscopy and gel electrophoresis. Preferably the diazo group is linked to the separation medium trough a linker group consisting of a chemically, physically or photolytically labile linker.

The present invention also relates to a method for the determining the presence or absence of phosphorylated proteins or peptides from a protein or peptide mixture by comparison with a reference standard phosphorylated or non-phosphorylated protein or peptide which comprises:

(a) providing a protein or peptide mixture comprising the phosphorylated proteins or peptides;

(b) protecting any carboxylate groups in the mixture of step (a) by reaction with protecting agent;

(c) reacting the mixture of step (b) with a diazo group-substituted organic moiety linked to a separation medium to bind a phosphate group of the phosphorylated protein or peptide to the organic moiety in place of the diazo group;

(d) separating the phosphorylated proteins or peptides bound to the separation medium from the mixture;

(e) releasing the bound phosphorylated proteins or peptides from the separation medium; and (f) determining the presence or absence of the separated phosphorylated protein or peptide by comparison with the reference standard.

The present invention also relates to a method for the compositional analysis of phosphorylated proteins or peptides from a protein or peptide mixture by comparison with a reference standard phosphorylated or non-phosphorylated protein or polypeptide which comprises:

(a) providing a protein or peptide mixture comprising the phosphorylated proteins or peptides;

(b) protecting any carboxylate groups in the mixture of step (a) by reaction with a protection agent;

(c) reacting the mixture of step (b) with a diazo group-substituted organic moiety linked to a separation medium to bind a phosphate group of the phosphorylated protein or peptide to the organic moiety in place of the diazo group;

(d) separating the phosphorylated proteins or peptides bound to the separation medium from the mixture;

(e) releasing the bound phosphorylated proteins or peptides from the separation medium; and (f) determining the presence or absence of the separated phosphorylated protein or peptide by comparison with the reference standard.

The present invention further relates to a kit for separating of phosphorylated proteins or peptides from a protein or peptide mixture which comprises:

(a) a diazo group-substituted organic moiety linked to a separation medium wherein a phosphate group of the phosphorylated protein or peptide binds to the organic moiety in place of the diazo group; and (b) instructions enabling use of the kit with the use of a reagent, if necessary, to protect any carboxylic acid group in the protein or peptide mixture.

The present invention also relates to a kit for separating phosphorylated proteins and peptides from a protein or peptide mixture which comprises:

(a) a protein or peptide mixture comprising the phosphorylated proteins or peptides; and (b) a reference standard phosphorylated or non-phosphorylated, protein or peptide for determining the presence or absence of the phosphorylated protein or peptide in the mixture. Preferably the protein or peptide mixture in step (a) has been purified to remove unwanted proteins or peptides. Preferably the protein or peptide mixture in step (a) has been purified to remove unwanted proteins or peptides. Preferably the kit includes a reagent for purifying the protein or peptide mixture. The kit also includes a reagent for purifying the protein or peptide mixture.

The present invention also relates to a method for the separation of phosphorylated proteins or phosphorylated peptides from a protein or peptide mixture which comprises:

(a) providing a protein or peptide mixture comprising the phosphorylated proteins or phosphorylated peptides;

(b) protecting any carboxylate groups in the mixture of step (a) by reaction with an esterification agent, an amination agent, a thiolating agent or an olefin to form structures of the formulas:

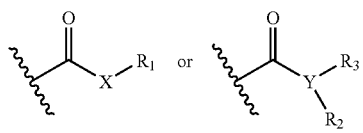

wherein x comprises oxygen or sulfur, Y is nitrogen and R1, R2 and R3 are selected from the group consisting of hydrogen, an alkyl, acyl or aryl moiety and mixtures thereof.

(c) reacting the mixture of step (b) with a diazo group-substituted organic moiety linked to a separation medium to bind a phosphate group of the phosphorylated protein or phosphorylated peptide to the organic moiety in place of the diazo group;

(d) separating the phosphorylated proteins or phosphorylated peptides bound to the separation medium from the mixture; and (e) releasing the bound phosphorylated proteins or phosphorylated peptides from the separation medium.

The present invention also relates to a method for the compositional analysis of phosphorylated proteins or peptides from a protein or peptide mixture which comprises:

(a) providing a protein or peptide mixture comprising the phosphorylated proteins or phosphorylated peptides;

(b) protecting any carboxylate groups in the mixture of step (a) by reaction with an esterification agent, an amination agent, a thiolating agent or an olefin to form structures of the formulas:

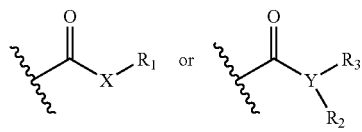

wherein X comprises oxygen or sulfur, Y is nitrogen and R1, R2 and R3 are selected from the group consisting of a hydrogen, an alkyl, acyl or aryl moiety and mixtures thereof;

(c) reacting the mixture of step (b) with an diazo group-substituted organic moiety linked to a separation medium to bind a phosphate group of the phosphorylated protein or phosphorylated peptide to the organic moiety in place of the diazo group;

(d) separating the phosphorylated proteins or phosphorylated peptides bound to the separation medium from the mixture;

(e) releasing the bound phosphorylated proteins or phosphorylated peptides from the separation medium; and (f) subjecting the released phosphorylated proteins or phosphorylated peptides in step (e) to chemical and physical analytical methods to determine the composition of the phosphorylated entities.

The present invention also relates to a method for the determining the presence or absence of phosphorylated proteins or phosphorylated peptides from a protein or peptide mixture by comparison with a reference standard which comprises:

(a) providing a protein or peptide mixture containing the phosphorylated proteins or phosphorylated peptides;

(b) protecting any carboxylate groups in the mixture of step (a) by reaction with an esterification agent, an amination agent, a thiolating agent or an olefin to form structures of the formulas:

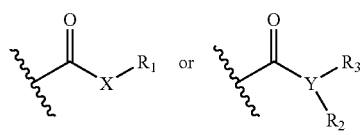

wherein X comprises oxygen or sulfur, Y is nitrogen and R1, R2 and R3 are selected from the group consisting of hydrogen, an alkyl, acyl or aryl moiety and mixtures thereof;

(c) reacting the mixture of step (b) with a diazo group-substituted organic moiety linked to a separation medium to bind a phosphate group of the phosphorylated protein or phosphorylated peptide to the organic moiety in place of the diazo group;

(d) separating the phosphorylated proteins or phosphorylated peptides bound to the separation medium from the mixture;

(e) releasing the bound phosphorylated proteins or phosphorylated peptides from the separation medium; and
(f) determining the presence or absence of the separated phosphorylated protein or phosphorylated peptide by comparison with the reference standard.

The present invention also relates to a method for the compositional analysis of phosphorylated proteins or phosphorylated peptides from a protein or peptide mixture by comparison with a reference standard which comprises:
(a) providing a protein or peptide mixture containing the phosphorylated proteins or phosphorylated peptides;
(b) protecting any carboxylate groups in the mixture of step (a) by reaction with an esterification agent, an amination agent, a thiolating agent or an olefin to form structures of the formulas:

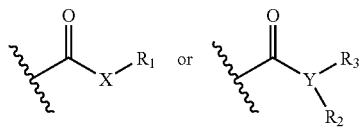

wherein X comprises oxygen or sulfur, Y is nitrogen and R1, R2 and R3 are selected from the group consisting of hydrogen, an alkyl, acyl or aryl moiety and mixtures thereof;
(c) reacting the mixture of step (b) with a diazo group-substituted organic moiety linked to a separation medium to bind a phosphate group of the phosphorylated protein or phosphorylated peptide to the organic moiety in place of the diazo group;
(d) separating the phosphorylated proteins or phosphorylated peptides bound to the separation medium from the mixture;
(e) releasing the bound phosphorylated proteins or phosphorylated peptides from the separation medium; and
(f) determining the presence or absence of the separated phosphorylated protein or phosphorylated peptide by comparison with the reference standard.

The present invention also relates to a method for the separation of phosphorylated proteins or phosphorylated peptides from a protein or peptide mixture which comprises:
(a) providing a protein or peptide mixture comprising the phosphorylated proteins or phosphorylated peptides;
(b) protecting any carboxylate groups in the mixture of step (a) by reaction with an esterification agent, an amination agent, a thiolating agent or an olefin to form structures of the formulas:

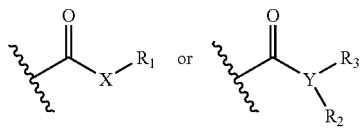

wherein X comprises oxygen or sulfur, Y comprises is nitrogen and R1, R2 and R3 are selected from the group consisting of hydrogen, an alkyl, acyl or aryl moiety and mixtures thereof;
(c) reacting the mixture of step (b) with a diazo group-substituted organic moiety to bind a phosphate group of the phosphorylated protein or phosphorylated peptide to the organic moiety in place of the diazo group;
(d) linking the functionalized phosphorylated proteins or phosphorylated peptides of step (c) to a separation medium;
(e) separating the separation medium from the mixture; and
(f) releasing the bound phosphorylated proteins or phosphorylated peptides from the separation medium.

The present invention also relates to a method for the compositional analysis of phosphorylated proteins or phosphorylated peptides from a protein or peptide mixture which comprises:
(a) providing a protein or peptide mixture comprising the phosphorylated proteins or phosphorylated peptides;
(b) protecting any carboxylate groups in the mixture of step (a) by reaction with an esterification agent, an amination agent, a thiolating agent or an olefin to form structures of the formulas:

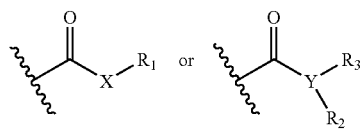

wherein x comprises oxygen or sulfur, Y is nitrogen and R1, R2 and R3 are selected from the group consisting of hydrogen, an alkyl, acyl, or aryl moiety and mixtures thereof;
(c) reacting the mixture of step (b) with a diazo group-substituted organic moiety to bind a phosphate group of the phosphorylated protein or phosphorylated peptide to the organic moiety in place of the diazo group;
(d) linking the functionalized phosphorylated proteins or phosphorylated peptides of step (c) to a separation medium;
(e) separating the separation medium from the mixture;
(f) releasing the bound phosphorylated proteins or phosphorylated peptides from the separation medium; and
(g) subjecting the released phosphorylated proteins or phosphorylated peptides in step (e) to chemical and physical analytical methods to determine the composition of the phosphorylated entities. Preferably the mixture of peptides or proteins in step (a) is obtained from sources comprising: cell extracts, cell extracts obtained through cell lysis and the digestion products thereof. The protein or peptide mixture in step (a) has been enriched by a method selected from the group comprising immuno-precipitation, gel electrophoresis, chromatography, size exclusion chromatography, affinity chromatography centrifugation, and mixtures thereof. The carboxylate groups of the protein or peptide are protected from reaction with the diazo groups by reaction methods selected from the group comprising:
(a) esterification by an esterifying agent selected from the group comprising alkyl alcohols, aryl alcohols, alkyl halide, aryl halide, alkyl triflate, aryl triflate, and mixtures thereof;
(b) amination by an amidating agent selected from the group comprising an alkyl amine or aryl amine; and
(c) esterification by isobutylene catalyzed by a mineral acid. The protection of the carboxylate groups of the peptide or protein is carried out in an acidic anhydrous alcohol solution formed by the reaction of an acid chloride or anhydride with alcohols or by protection of the carboxylate groups with isobutylene catalyzed by a mineral acid. The diazo group used to bind a phosphate group of the phosphorylated protein or peptide with the loss of the $N_2$ has the general formulas:

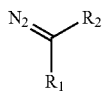

Diazo group and wherein $R_1$ and $R_2$ are selected from the group consisting of hydrogen, a carbonyl group, an ester, an amide, an aryl group, an alkyl group, an acyl group, an aryl group, an arylalkyl group, a heteroaryl group, a homocyclic ring containing 5-14 carbon atom members, a heterocyclic ring containing 4-12 ring members, organo halides, alkoxides, organo sulfoxides, organo sulfonates, organo phosphonates, and combinations thereof. The diazo group used to bind a phosphate group of the phosphorylated protein or phosphorylated peptide to the separation medium with the loss of the $N_2$ has the general formula:

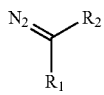

Diazo group and wherein $R_1$ is hydrogen and $R_2$ is a resonance stabilizing organic moiety. The diazo group is an α-diazo group prepared by diazotization of an amine functionality. The diazo group of the separation medium is an α-diazo group prepared by reaction of a diazoalkane with a

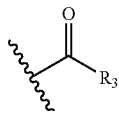

group bound to the separation medium wherein $R_3$ is selected from the group comprising an amide, a halide, an alkoxide, a thiol, an amine, amide, trichloromethyl, trifluoromethyl, acid, succinamide, cyano, azide, sulfonate, phosphite sulfite or derivatives thereof. The diazo group is linked to the separation medium trough a linker group comprising alkyl groups, alkylaryl groups (Wang-type linkers), polyethylene glycol (PEG), bis 2-acrylamide based PEG co-polymers (PEGA), Rink amides and derivatives and combinations thereof. The separation medium is selected from the group comprising: a resin; a porous resin; a polymer; a thermomorphic polymer; a metal oxide; a metal hydroxide; a mesoporous metal oxide; a mesoporous metal hydroxide; a metal; a layered silicate clay, a layered metal phosphate; a layered metal phosphonate; and combinations thereof. The separation medium is in thin-film, powdered, bead, gel, foam, sponge, fibrous or liquid form. The the bound phosphorylated proteins or phosphorylated peptides are released from the separation medium by methods comprising chemical reaction, thermal reaction, photochemical reaction, and combinations thereof. The bound phosphorylated proteins or phosphorylated peptides are released from the separation medium through chemical reaction with an acid or a base. The the bound phosphorylated proteins or phosphorylated peptides are released from the separation medium by reaction with an acid selected from the group comprising mineral acids, carboxylic acids, and halogenated carboxylic acids. The acids of claim 54 selected from the group comprising hydrochloric acid, sulfuric acid, phosphoric acid, acetic acid and trifluoroacetic acid. The bound phosphorylated proteins or phosphorylated peptides are released from the separation medium by reaction with a base selected from the group comprising sodium hydroxide, ammonium hydroxide, and buffers at a pH value >7. The the bound phosphorylated proteins or phosphorylated peptides are released from the separation medium by physical methods selected from the group comprising ablation and sublimation. The the bound phosphorylated proteins or phosphorylated peptides are released from the separation medium by photolytical means through irradiation of the separation medium with light of different wavelengths. The the diazo group is bound to the separation medium through a linker group that is chemically, thermally or photolytically labile.

The present invention also relates to a kit for the separating of phosphorylated proteins or phosphorylated peptides from a protein or peptide mixture wherein the kit comprises:

(a) a separation medium wherein a diazo group-substituted organic moiety is covalently linked to the separation medium and wherein the separation medium is effective in binding a phosphate group of the phosphorylated protein or the phosphorylated peptide to the organic moiety in place of the diazo group; and (b) instructions enabling use of the kit including methods for reacting the mixture with a diazo group-substituted organic moiety linked to a separation medium to bind a phosphate group of the phosphorylated protein or phosphorylated peptide to the organic moiety in place of the diazo group, use of reagents and methods to protect any carboxylic acid groups in the protein or peptide mixture, use of reagents and methods for separating the phosphorylated proteins or phosphorylated peptides bound to the separation medium from the mixture, and use of reagents and methods for releasing the bound phosphorylated proteins or peptides from the separation medium.

The present invention also relates to a kit for the compositional analysis of phosphorylated proteins or phosphorylated peptides from a protein or peptide mixture wherein the kit comprises:

(a) a separation medium wherein a diazo group-substituted organic moiety is covalently linked to the separation medium and wherein the separation medium is effective in binding a phosphate group of the phosphorylated protein or the phosphorylated peptide to the organic moiety in place of the diazo group;

(b) instructions enabling use of the kit including methods for reacting the mixture with a diazo group-substituted organic moiety linked to a separation medium to bind a phosphate group of the phosphorylated protein or phosphorylated peptide to the organic moiety in place of the diazo group, use of reagents and methods to protect any carboxylic acid groups in the protein or peptide mixture, use of reagents and methods for separating the phosphorylated proteins or phosphorylated peptides bound to the separation medium from the mixture, and use of reagents and methods for releasing the bound phosphorylated proteins or phosphorylated peptides from the separation medium; and (c) instructions enabling the determination of the composition of the released phosphorylated proteins or phosphorylated peptides in step (b) by chemical and physical analytical methods.

The invention also relates to a kit for the separating of phosphorylated proteins or phosphorylated peptides from a protein or peptide mixture wherein the kit comprises:

(a) a diazo group-substituted organic moiety effective in binding a phosphate group of the phosphorylated protein or phosphorylated peptide to the organic moiety in place of the diazo group;

(b) a separation medium effective in linking the functionalized phosphorylated proteins or phosphorylated peptides of step (a); and (c) instructions enabling use of the kit including methods for reacting the mixture with a diazo group-substituted organic moiety and use of reagents and methods to link of the functionalized phosphorylated proteins or phosphorylated peptides of step (a) to a separation medium, use of reagents and methods to protect any carboxylic acid groups in the protein or peptide mixture, use of reagents and methods for separating the phosphorylated proteins or phosphorylated peptides bound to the separation medium from the mixture, and use of reagents and methods for releasing the bound phosphorylated proteins or peptides from the separation medium.

The present invention also relates to a kit for the compositional analysis of phosphorylated proteins or phosphorylated peptides from a protein or peptide mixture wherein the kit comprises:

(a) a diazo group-substituted organic moiety effective in binding a phosphate group of the phosphorylated protein or phosphorylated peptide to the organic moiety in place of the diazo group;

(b) a separation medium effective in linking the functionalized phosphorylated proteins or phosphorylated peptides of step (a);

(c) instructions enabling use of the kit including methods for reacting the mixture with a diazo group-substituted organic moiety and use of reagents and methods to link of the functionalized phosphorylated proteins or phosphorylated peptides of step (a) to a separation medium, use of reagents and methods to protect any carboxylic acid groups in the protein or peptide mixture, use of reagents and methods for separating the phosphorylated proteins or phosphorylated peptides bound to the separation medium from the mixture, and use of reagents and methods for releasing the bound phosphorylated proteins or peptides from the separation medium; and (d) instructions enabling the determination of the composition of the released phosphorylated proteins or phosphorylated peptides in step (c) by chemical and physical analytical methods. Preferably the instructions provide for the separation and compositional analysis of phosphorylated peptides and phosphorylated proteins obtained from cell extracts, cell extracts obtained through cell lysis and the digestion products thereof. Preferably the instructions provide for the separation and compositional analysis of phosphorylated peptides and phosphorylated proteins enriched through methods selected from the group comprising immuno-precipitation, gel electrophoresis, chromatography, size exclusion chromatography, affinity chromatography centrifugation, and mixtures thereof. Preferably the instructions of part (c) which enable the determination of the composition of the released phosphorylated proteins or phosphorylated peptides by analytical methods selected from the group comprising Edman degradation, mass spectroscopy, MALDI mass spectroscopy, nuclear magnetic resonance spectroscopy and gel electrophoresis. Preferably the kits include reagents and instructions for the separating of phosphorylated proteins or phosphorylated peptides from mixtures of proteins and peptides from sources comprising: cell extracts, cell extracts obtained through cell lysis and the digestion products thereof. Preferably the kits include reagents and instructions for enriching the phosphorylated protein or phosphorylated peptide mixture through methods selected from the group comprising immuno-precipitation, gel electrophoresis, chromatography, size exclusion chromatography, affinity chromatography centrifugation, and mixtures thereof.

For instance, thermomorphic polymers, which have been recently recognized as a new generation of separation media [D. E. Bergbreiter, Medicinal Research Reviews 1999, 19(5), 439-450] can be miscible with polar solvents at one temperature but immiscible at a higher or lower temperature. In the miscible state the polymer is readily accessible for reaction with reagents in polar solution and in the immiscible state, the thermomorphic polymer is easily separated from the polar solvent.

Polystyrene resins, as well as many other polymer resins, are widely recognized as separation media for the immobilization of organic reagents and catalysts. The applications of such resins include uses as electrophile and nucleophile scavengers, metal scavengers, polymer-supported bases and acids, polymer-supported oxidizing and reducing agents, among other agents. Several examples of commercially available versions of such functionalized resins are provided on the following websites:

http://www.sigmaaldrich.com/aldrich/brochure/al che mfile v4 no1.pdf http://www.emdbiosciences.com/Products/BrowseProductsByCategory.asp?catid=515

Polymer resins also are useful as supports for the reagents described in the present invention for the separation of phosphorylated proteins and peptides from complex mixtures. In most cases the amount of organofunctional groups on these commercially available resins is in the range 0.4 to 4 mmole per gram. However, they may not be the preferred immobilization medium for the separation of phosphorylated proteins from complex mixtures. Not all of the organofunctional groups immobilized on a polymer resin can be expected to be available for reaction with phosphorylated proteins or peptides from solution. Limited swelling of the resin matrix by the aqueous solvent containing the phosphorylated protein or peptide can limit the number of accessible binding sites to a value well below the formal loading value. Nevertheless, such polymeric resins are useful immobilization matrices for the purposes of the present invention.

Included among the preferred separation media of the present invention are the organofunctional meso- to macroporous metal oxides. These materials typically have pore sizes between 2 and 100 nm, making nearly all of the surface functional groups available for reaction with reagents from solution. The pore walls of these materials can be constructed of siliceous or non-siliceous backbones containing metal-oxygen-metal bonds and pendant organo groups that are accessible for reaction with guest species adsorbed in the pores and channels of the structure. [A. Stein, Adv. Mater. 2000, 12(19, 1403-1419; A. Sayari; S. Hamoudi, Chem.

Mater. 2001, 13(10), 3151-3168; F. Schueth, Chem. Mater. 2001, 13(10), 3184-3195; El Haskouri et al., European J. Inorg. Chem., 2004 (9), 1804-1807; M. C. Burleigh et al., Colloid Polym. Sci. 2004, 282(7), 728-733.] Organofunctional meso- to macro-porous oxides that contain pendant diazo functional groups are especially preferred separation media. Organofunctional derivatives of metal oxide gels, such as organofunctional silica gels, also are suitable separation media. Examples of organofunctional silica gels are provided at the website www.silicycle.com. Organofunctional silica gels that contain pendant diazo functional groups are preferred separation media.

Layered structures with substantial surface areas, such smectite clays in organic ion exchange form, layered phosphonates, and organofunctional layered metal hydroxides are also materials suitable for use as separation media for the purpose of this invention. Examples of these materials are provided in the following references: A. Clearfield, Z. Wang, J. Chem. Soc., Dalton Transactions 2002, (15), 2937-2947; A. I. Khan, I.; D. O'Hare, J. Mater. Chem. 2002, 12(11), 3191-3198; R. Barrer "Zeolites and Clay Minerals as Sorbents and Molecular Sieves". 1978, 496 pp. Publisher: (Academic, London, Engl.)]

Metals coated with a self-assembled monolayer or multilayers of organic molecules can also serve as separation media [N. Sandhyarani; T. Pradeep, International Reviews in Physical Chemistry (2003), 22(2), 221-262]. Gold coated with a monolayer of an organic thiol containing a diazo group is an especially suitable separation medium.

Preferably the bound phosphorylated proteins or peptides are released from the separation medium by a chemical reaction, a thermal reaction, a photochemical reaction, an enzymatic reaction or combinations thereof. Preferably the bound phosphorylated proteins or peptides are released from the separation medium through chemical reaction with an acid or a base. Preferably the bound phosphorylated proteins or peptides are released from the separation medium by reaction with an acid selected from the group consisting of mineral acids, carboxylic acids, and halogenated carboxylic acids. Preferably the acid is selected from the group consisting of hydrochloric acid, sulfuric acid, phosphoric acid, acetic acid and trifluoroacetic acid. Preferably the bound phosphorylated proteins or peptides are released from the separation medium by reaction with a base selected from the group consisting of sodium hydroxide, ammonium hydroxide, and buffers at a pH value >7. Preferably the bound phosphorylated proteins or peptides are released from the separation medium by physical methods selected from the group consisting of ablation and sublimation. Preferably the bound phosphorylated proteins or peptides are released from the separation medium by photolytical means by treatment of the separation medium with different wavelengths of light. Preferably the bound phosphorylated proteins or peptides are released from the separation medium by reaction by an enzymatic reaction with enzymes selected from the group consisting of esterases, phosphatase, lipases or proteases.

Preferably the diazo group is linked to the separation medium through a linker group consisting of a chemically, physically or photolytically labile linker.

The present invention relates to a kit for the separating of phosphorylated proteins or peptides from a protein or peptide mixture which comprises:
  (a) a diazo group-substituted organic moiety linked to a separation medium; and
  (b) instructions enabling use of the kit including methods for reacting the mixture with a diazo group-substituted organic moiety linked to a separation medium to bind a phosphate group of the phosphorylated protein or peptide to the organic moiety in place of the diazo group, use of an esterifying reagent to esterify any carboxylic acid groups in the protein or peptide mixture, use of reagents and methods for separating the phosphorylated proteins or peptides bound to the separation medium from the mixture, and use of reagents and methods for releasing the bound phosphorylated proteins or peptides from the separation medium.

The present invention relates to a kit for the compositional analysis of phosphorylated proteins or peptides from a protein or peptide mixture which comprises:
  (a) a diazo group-substituted organic moiety linked to a separation medium;
  (b) instructions enabling use of the kit, including instructions for reacting the mixture with an diazo group substituted organic moiety linked to a separation medium to bind a phosphate group of the phosphorylated protein or peptide to the organic moiety in place of the diazo group, use of an esterifying reagent to esterify any carboxylic acid groups in the protein or peptide mixture, use of reagents and methods for separating the phosphorylated proteins or peptides bound to the separation medium from the mixture and use of reagents and methods for releasing the bound phosphorylated proteins or peptides from the separation medium, and
  (c) instructions enabling the determination of the composition of the released phosphorylated proteins or peptides in step (b) by chemical and physical analytical methods.

Preferably the instructions provide for the separation and compositional analysis of peptides or proteins from living cells. Preferably the analytical methods of step (c) are selected from the group consisting of Edman degradation, mass spectroscopy, MALDI mass spectroscopy, nuclear magnetic resonance spectroscopy and gel electrophoresis.

The present invention relates to a method for the determining the presence or absence of phosphorylated proteins or peptides from a protein or peptide mixture by comparison with a reference standard phosphorylated or non-phosphorylated protein or peptide which comprises:
  (a) providing a protein or peptide mixture comprising the phosphorylated proteins or peptides;
  (b) protecting any carboxylate groups in the mixture of step (a) by reaction with protecting agent;
  (c) reacting the mixture of step (b) with a diazo group-substituted organic moiety linked to a separation medium to bind a phosphate group of the phosphorylated protein or peptide to the organic moiety in place of the diazo group;
  (d) separating the phosphorylated proteins or peptides bound to the separation medium from the mixture;
  (e) releasing the bound phosphorylated proteins or peptides from the separation medium; and
  (f) determining the presence or absence of the separated phosphorylated protein or peptide by comparison with the reference standard.

The present invention relates to a method for the compositional analysis of phosphorylated proteins or peptides from a protein or peptide mixture by comparison with a reference standard phosphorylated or non-phosphorylated protein or polypeptide which comprises:
  (a) providing a protein or peptide mixture comprising the phosphorylated proteins or peptides;
  (b) protecting any carboxylate groups in the mixture of step (a) by reaction with a protection agent;

(c) reacting the mixture of step (b) with a diazo group-substituted organic moiety linked to a separation medium to bind a phosphate group of the phosphorylated protein or peptide to the organic moiety in place of the diazo group;
(d) separating the phosphorylated proteins or peptides bound to the separation medium from the mixture;
(e) releasing the bound phosphorylated proteins or peptides from the separation medium; and
(f) determining the presence or absence of the separated phosphorylated protein or peptide by comparison with the reference standard.

The present invention relates to a kit for separating of phosphorylated proteins or peptides from a protein or peptide mixture which comprises:
(a) a diazo group-substituted organic moiety linked to a separation medium wherein a phosphate group of the phosphorylated protein or peptide binds to the organic moiety in place of the diazo group; and
(b) instructions enabling use of the kit with the use of a reagent, if necessary, to protect any carboxylic acid group in the protein or peptide mixture.

The present invention relates to a kit for separating phosphorylated proteins and peptides from a protein or peptide mixture which comprises:
(a) a protein or peptide mixture comprising the phosphorylated proteins or peptides; and
(b) a reference standard phosphorylated or non-phosphorylated, protein or peptide for determining the presence or absence of the phosphorylated protein or peptide in the mixture.

Further, the present invention relates to a method for the separation and compositional analysis of phosphorylated proteins or phosphorylated peptides from a protein or peptide mixture which comprises:
(a) a protein or peptide mixture comprising the phosphorylated proteins or phosphorylated peptides of unknown chemical composition;
(b) protecting any carboxylate groups in the mixture of step (a) by reaction with an esterification agent, an amination agent, thiolating agent or olefins generating structures of the structures

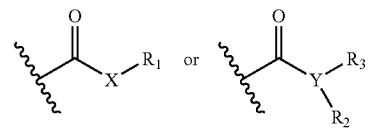

wherein X comprises oxygen or sulfur, Y is nitrogen and R1, R2 and R3 are selected from the group consisting of hydrogen, an alkyl, acyl or aryl moiety and mixtures thereof.
(c) reacting the mixture of step (b) with a diazo group-substituted organic moiety to bind a phosphate group of the phosphorylated protein or phosphorylated peptide to the organic moiety in place of the diazo group;
(d) linking the functionalized phosphorylated proteins or phosphorylated peptides of step (c) to a separation medium similar to the example shown below;

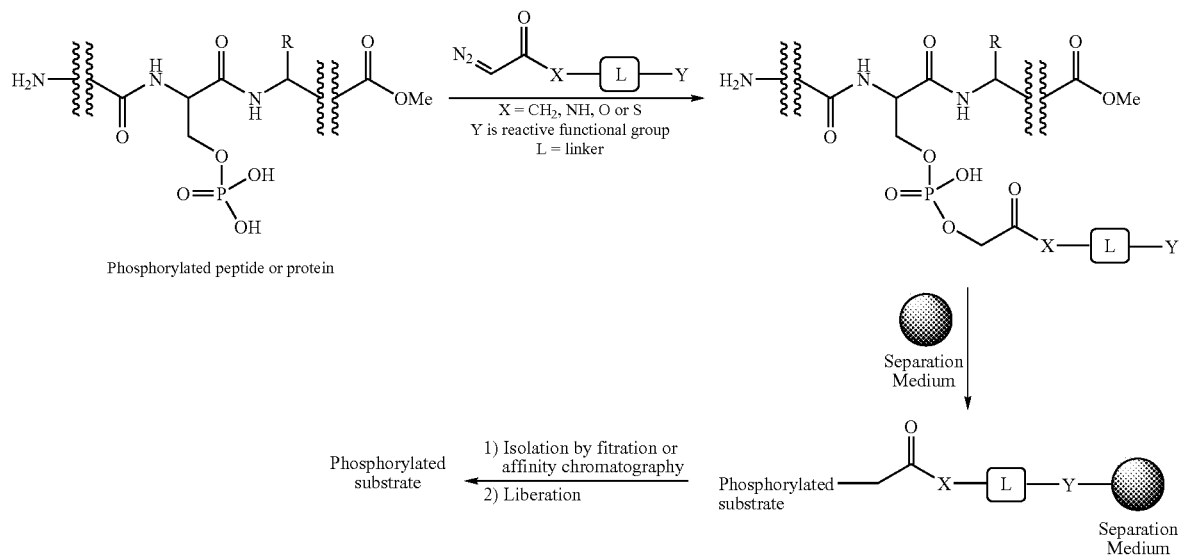

Preferably the protein or peptide mixture in step (a) has been purified to remove unwanted proteins or peptides. Preferably the protein or peptide mixture in step (a) has been purified to remove unwanted proteins or peptides. Preferably the kit includes a reagent for purifying the protein or peptide mixture. Preferably the kit includes a reagent for purifying the protein or peptide mixture. The diazo organic moiety an be reacted with the protein prior to coupling to the separation medium.

(e) separating the separation medium from the mixture; and
(f) releasing the bound phosphorylated proteins or phosphorylated peptides from the separation medium.

The present invention relates to a method for the separation of phosphorylated proteins or phosphorylated peptides from a protein or peptide mixture which comprises:
(a) providing a protein or peptide mixture comprising the phosphorylated proteins or phosphorylated peptides;

(b) protecting any carboxylate groups in the mixture of step (a) by reaction with an esterification agent, an amination agent, a thiolating agent or an olefin to form structures of the structures

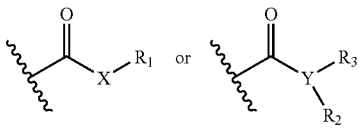

wherein X comprises oxygen or sulfur, Y comprises is nitrogen and R1, R2 and R3 are selected from the group consisting of hydrogen, an alkyl, acyl or aryl moiety and mixtures thereof;

(c) reacting the mixture of step (b) with a diazo group-substituted organic moiety to bind a phosphate group of the phosphorylated protein or phosphorylated peptide to the organic moiety in place of the diazo group;

(d) linking the functionalized phosphorylated proteins or phosphorylated peptides of step (c) to a separation medium;

(e) separating the separation medium from the mixture; and (f) releasing the bound phosphorylated proteins or phosphorylated peptides from the separation medium.

Further, the present invention relates to a method for the compositional analysis of phosphorylated proteins or phosphorylated peptides from a protein or peptide mixture which comprises:

(a) providing a protein or peptide mixture comprising the phosphorylated proteins or phosphorylated peptides;

(b) protecting any carboxylate groups in the mixture of step (a) by reaction with an esterification agent, an amination agent, a thiolating agent or an olefin to form structures of the structures

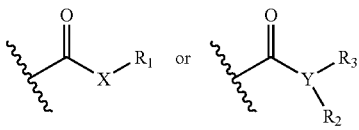

wherein x comprises oxygen or sulfur, Y is nitrogen and R1, R2 and R3 are selected from the group consisting of hydrogen, an alkyl, acyl, or aryl moiety and mixtures thereof;

(c) reacting the mixture of step (b) with a diazo group-substituted organic moiety to bind a phosphate group of the phosphorylated protein or phosphorylated peptide to the organic moiety in place of the diazo group;

(d) linking the functionalized phosphorylated proteins or phosphorylated peptides of step (c) to a separation medium;

(e) separating the separation medium from the mixture;

(f) releasing the bound phosphorylated proteins or phosphorylated peptides from the separation medium; and (g) subjecting the released phosphorylated proteins or phosphorylated peptides in step (e) to chemical and physical analytical methods to determine the composition of the phosphorylated entities. Preferably the mixture of peptides or proteins in step (a) is obtained from sources comprising: cell extracts, cell extracts obtained through cell lysis and the digestion products thereof.

Preferably the protein or peptide mixture in step (a) has been enriched by a method selected from the group comprising immuno-precipitation, gel electrophoresis, chromatography, size exclusion chromatography, affinity chromatography centrifugation, and mixtures thereof. Preferably the carboxylate groups of the protein or peptide are protected from reaction with the diazo groups by reaction methods selected from the group comprising:

(a) esterification by an esterifying agent selected from the group comprising alkyl alcohols, aryl alcohols, alkyl halide, aryl halide, alkyl triflate, aryl triflate, and mixtures thereof;

(b) amination by an amidating agent selected from the group comprising an alkyl amine or aryl amine; and (c) esterification by isobutylene catalyzed by a mineral acid. Preferably the protection of the carboxylate groups of the peptide or protein is carried out in an acidic anhydrous alcohol solution formed by the reaction of an acid chloride or anhydride with alcohols or by protection of the carboxylate groups with isobutylene catalyzed by a mineral acid. Preferably the diazo group used to bind a phosphate group of the phosphorylated protein or peptide with the loss of the $N_2$ has the general structure

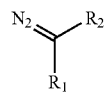

Diazo group and wherein $R_1$ and $R_2$ are selected from the group consisting of hydrogen, a carbonyl group, an ester, an amide, an aryl group, an alkyl group, an acyl group, an aryl group, an arylalkyl group, a heteroaryl group, a homocyclic ring containing 5-14 carbon atom members, a heterocyclic ring containing 4-12 ring members, organo halides, alkoxides, organo sulfoxides, organo sulfonates, organo phosphonates, and combinations thereof. Preferably the diazo group used to bind a phosphate group of the phosphorylated protein or phosphorylated peptide with the loss of the $N_2$ has the general structure

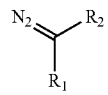

Diazo group and wherein $R_1$ is hydrogen and $R_2$ is a resonance stabilizing organic moiety. Preferably the diazo group is an α-diazo group prepared by diazotization of an amine functionality. Preferably the diazo group is an α-diazo group prepared by reaction of a diazoalkane with a

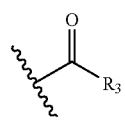

group bound to the separation medium wherein $R_3$ is selected from the group comprising an amide, a halide, an alkoxide, a thiol, an amine, amide, trichloromethyl, trifluoromethyl, acid, succinamide, cyano, azide, sulfonate, phosphite sulfite or derivatives thereof. Preferably the diazo group is linked to the separation medium through a linker group comprising alkyl groups, alkylaryl groups (Wang-type linkers), polyethylene glycol (PEG), bis 2-acrylamide based PEG co-polymers (PEGA), Rink amides and derivatives and combinations thereof. Preferably the separation medium is selected from the group comprising: a resin; a porous resin; a polymer; a thermomorphic polymer; a metal oxide; a metal hydroxide; a mesoporous metal oxide; a mesoporous metal hydroxide; a metal; a layered silicate clay, a layered metal phosphate; a layered metal phosphonate; and combinations thereof. Preferably the separation medium is in thin-film, powdered, bead, gel, foam, sponge, fibrous or liquid form. Preferably the diazo group is bound to the separation medium through a linker group that is chemically, thermally or photolytically labile.

The present invention relates to a kit for the separating of phosphorylated proteins or phosphorylated peptides from a protein or peptide mixture wherein the kit comprises:
  (a) a diazo group-substituted organic moiety effective in binding a phosphate group of the phosphorylated protein or phosphorylated peptide to the organic moiety in place of the diazo group;
  (b) a separation medium effective in linking the functionalized phosphorylated proteins or phosphorylated peptides of step (a); and
  (c) instructions enabling use of the kit including methods for reacting the mixture with a diazo group-substituted organic moiety and use of reagents and methods to link of the functionalized phosphorylated proteins or phosphorylated peptides of step (a) to a separation medium, use of reagents and methods to protect any carboxylic acid groups in the protein or peptide mixture, use of reagents and methods for separating the phosphorylated proteins or phosphorylated peptides bound to the separation medium from the mixture, and use of reagents and methods for releasing the bound phosphorylated proteins or peptides from the separation medium.

Preferably the present invention relates to a kit for the compositional analysis of phosphorylated proteins or phosphorylated peptides from a protein or peptide mixture wherein the kit comprises:
  (a) a diazo group-substituted organic moiety effective in binding a phosphate group of the phosphorylated protein or phosphorylated peptide to the organic moiety in place of the diazo group;
  (b) a separation medium effective in linking the functionalized phosphorylated proteins or phosphorylated peptides of step (a);
  (c) instructions enabling use of the kit including methods for reacting the mixture with a diazo group-substituted organic moiety and use of reagents and methods to link of the functionalized phosphorylated proteins or phosphorylated peptides of step (a) to a separation medium, use of reagents and methods to protect any carboxylic acid groups in the protein or peptide mixture, use of reagents and methods for separating the phosphorylated proteins or phosphorylated peptides bound to the separation medium from the mixture, and use of reagents and methods for releasing the bound phosphorylated proteins or peptides from the separation medium; and
  (d) instructions enabling the determination of the composition of the released phosphorylated proteins or phosphorylated peptides in step (c) by chemical and physical analytical methods. Preferably the instructions provide for the separation and compositional analysis of phosphorylated peptides and phosphorylated proteins obtained from cell extracts, cell extracts obtained through cell lysis and the digestion products thereof. Preferably the instructions provide for the separation and compositional analysis of phosphorylated peptides and phosphorylated proteins enriched through methods selected from the group comprising immuno-precipitation, gel electrophoresis, chromatography, size exclusion chromatography, affinity chromatography centrifugation, and mixtures thereof. Preferably the instructions of part (c) which enable the determination of the composition of the released phosphorylated proteins or phosphorylated peptides by analytical methods selected from the group comprising Edman degradation, mass spectroscopy, MALDI mass spectroscopy, nuclear magnetic resonance spectroscopy and gel electrophoresis. Preferably the kit includes reagents and instructions for the separating of phosphorylated proteins or phosphorylated peptides from mixtures of proteins and peptides from sources comprising: cell extracts, cell extracts obtained through cell lysis and the digestion products thereof. Preferably the kit includes reagents and instructions for enriching the phosphorylated protein or phosphorylated peptide mixture through methods selected from the group comprising immuno-precipitation, gel electrophoresis, chromatography, size exclusion chromatography, affinity chromatography centrifugation, and mixtures thereof.

EXAMPLE 1

In this example a known peptide mixture containing the tyrosine phosphorylated peptide angiotensin II [tyr $(OPO_3H_2)$] and the non-phosphorylated peptides, neurotensin, fibrinopeptide B and angiotensin I (Mixture I, Table 1) was selected as an example to illustrate the separation of phosphorylated proteins or peptides from a protein or peptide mixture according to the art of the present invention.

TABLE 1

Sequence and mass of peptide mixture I.

| Peptide | sequence | average mass | methylated |
|---|---|---|---|
| Ang II [tyrP]: | D-R-V-Y(P)-I-H-P-F-OH | 1126 | 1154 |
| Ang I: | D-R-V-Y-I-H-P-F-H-L-OH | 1296 | 1324 |
| FibB: | p-E-G-V-N-D-N-E-E-G-F-F-S-A-R-OH | 1552 | 1608 |
| Neur: | pyr-L-Y-E-N-L-P-R-R-P-Y-I-L-OH | 1673 | 1701 |

The separation of the phosphorylated peptide from the non-phosphorylated substrates was accomplished by first reacting the mixture with an esterifying reagent to esterify any carboxylic acid groups in the protein or peptide mixture, thereby preventing the carboxylate groups of the mixture from reacting with the diazo group of the separation medium. The esterification of the crude peptide mixture was accomplished by reaction of acetyl chloride and methanol. The in situ generation of the anhydrous methanolic hydrochloric acid solution (2N) quantitatively and selectively esterified the carboxylic acid residues of the mixture, but not the phosphate group, within a reaction time of 30-120 minutes at ambient temperature.

An alpha-diazo functionalized polystyrene resin, also known as an alpha-diazo functionalized Wang resin, wherein the benzylated polystyrene resin is referred to as Wang resin, was used as the medium to separate the phosphorylated component from the peptide mixture. The preparation of the resin is described in the literature by Tepe, one of the inventors. Exposure of the peptide mixture to an excess of the alpha-diazo-substituted resin (10 mg) to 500 fmol of the methylated peptide mixture in 500 microliter of dimethylformamide overnight linked the phosphorylated peptide to the resin through a covalent phosphate-carbon bond.

The unbound, non-phosphorylated peptides were washed away from the separation medium with dimethylformamide and methanol. The bound phosphorylated peptide was released from the separation medium by reacting the separation media with a mixture of trifluoroacetic acid (TFA) in water (9:1) for 2 hours, resulting in the methylated phosphorylated peptide product.

Alternatively, the release of the product with 10% $NH_4OH$ for 30 minutes results in the recovery of the de-methylated or deprotected phosphorylated peptide after evaporation of the solvent.

EXAMPLE 2

This example illustrates the analysis of phosphorylated peptides from a peptide mixture by MALDI-tof mass spectroscopy.

The peptide mixture I of Example 1 was methylated for 30 minutes with anhydrous methanolic hydrochloric acid (2N) generated in situ from acetylchloride in methanol. An aliquot of mixture I was subjected to MALDI-tof. Comparison of the mass spectra of the mixture before and after the esterification indicates that this treatment quantitatively esterified all of the carboxylic acids, but none of the phosphate moieties present in mixture I (FIG. 1). Mass increases of 14 units per carboxylic acid corresponded to all of the carboxylic acids found in each of the peptide substrates.

Exposure of an excess of the a α-diazo-substituted resin (10 mg) to 500 fmol of the methylated mixture I in 500 microliter dimethylformamide overnight, resulted in the formation of a covalent phosphopeptide-resin bond. The unbound peptides were washed away with dimethylformamide and methanol and the covalently bound phosphopeptides were subsequently liberated from the resin.

Cleavage of the phosphorylated substrate from the resin with 90% TFA for 2 hours provided the dimethylated angiotensin II tyrosine phosphate as the sole product (m/z=1155).

Figure 2:
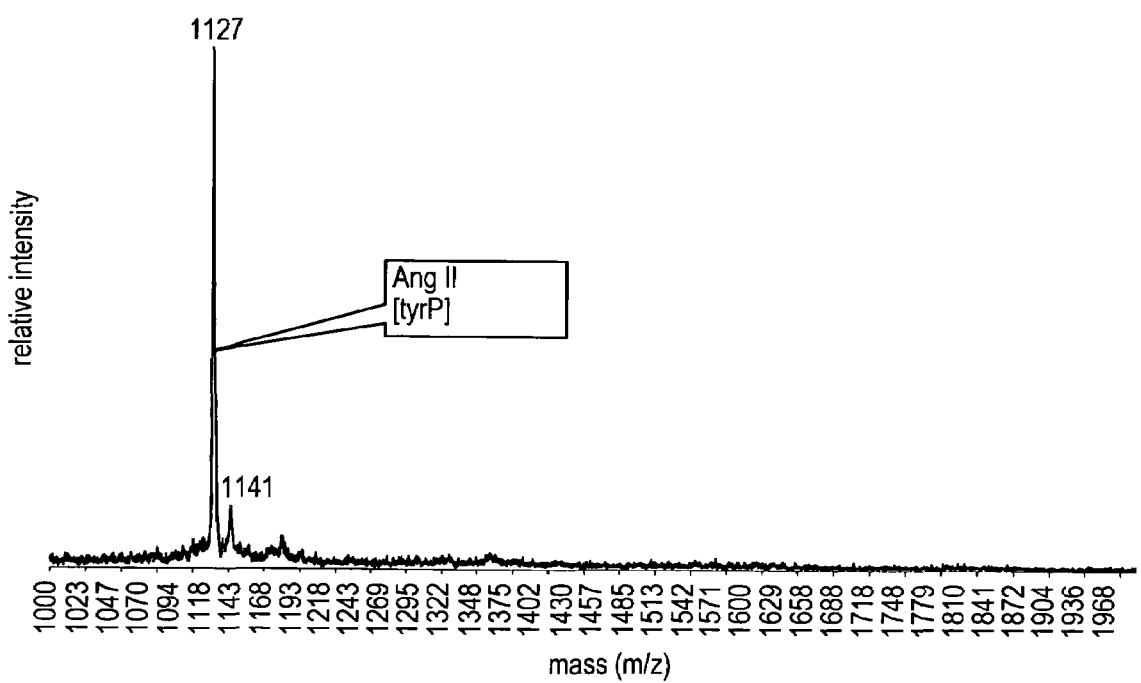

Alternatively, it was possible to liberate the phosphorylated peptide from the separation medium with 10% $NH_4OH$ for 30 minutes. This release procedure resulted in the recovery of the fully demethylated or deprotected angiotensin II tyrosine phosphate after evaporation of the solvent (FIG. 2).

The liberated peptides collected in the eluant were identified by MALDI-tof mass spectroscopy. In FIG. 2, the peak at m/z=1127 corresponds to angiotensin II tyrosine phosphate. The peak at m/z=1141 corresponds to the partial hydrolysis of the diester angiotensin II to the monomethyl ester.

EXAMPLE 3

The following example illustrates a method for the separation of phosphorylated peptides from a protein mixture and a method for the analysis of phosphorylated peptides from a peptide mixture by MALDI-tof mass spectroscopy and Edman degradation.

To evaluate the efficacy of the resin on a more complex peptide mixture the solid phase enrichment was performed on a chymotrysine digest of glycogen phosphorylase A (97 KDa).

Figure 3A:
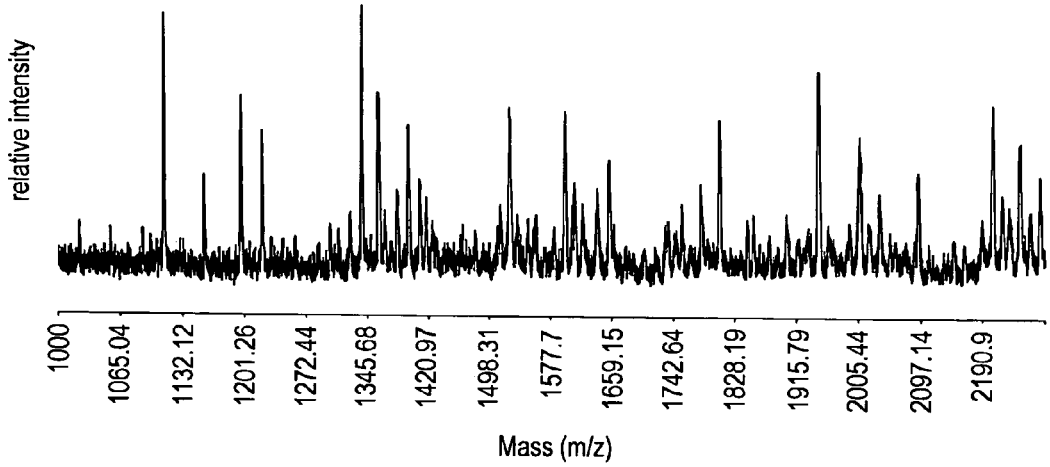
FIGS. 3A and 3B are mass spectra as described in Example 3.
Figure 3B:
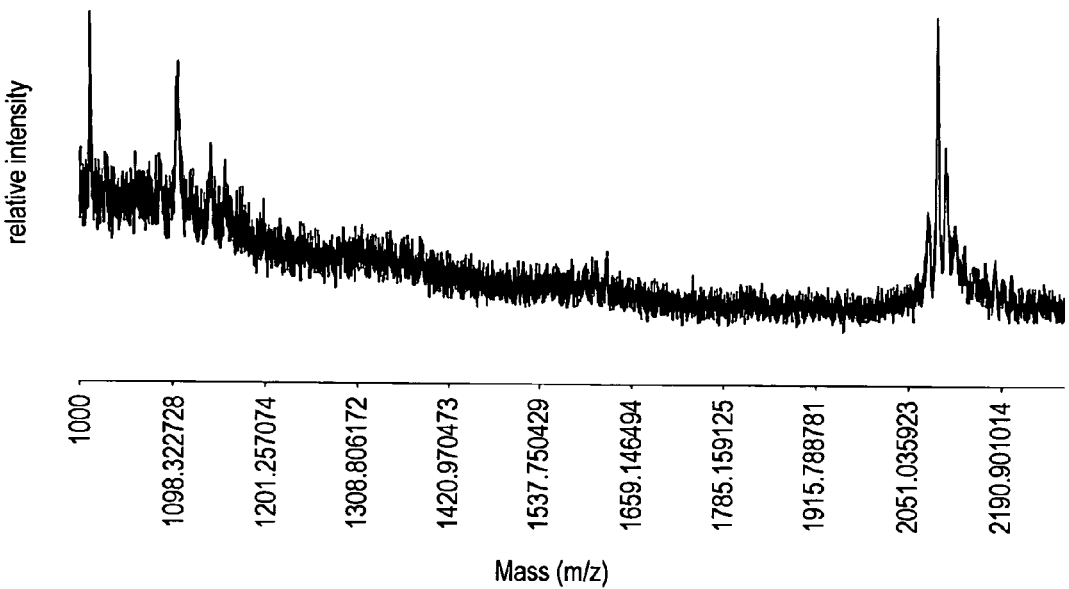

The protein was digested with chymotrypsine (1:200 quantity of protein by weight) at pH 7.9-9.0 for 5 hours at room temperature to form peptide fragments. The peptides were dried completely. The fragmented protein products were then subjected to esterification by reaction with anhydrous methanol as described in Example 1. The MALDI-tof mass spectrum of the methylated crude product is shown in FIG. 3a. The crude methylated peptide mixture was subjected to the enrichment and the crude product isolated from the resin was analyzed by MALDI-tof (FIG. 3b) to observe the enriched phosphorylated fragments. As is clearly illustrated by the mass spectral results, the eluant contained two major products (m/z 2094.02 and 1104.30). The crude product was subjected to MS/MS fragmentation as well as Edman degradation at the proteomics facility at Michigan State University for verification of the anticipated phosphorylation domain of glycogen phosphorylase A. The peptide sequences corresponded to the phosphorylated peptide sequences containing the phosphorylated ser[14] at different pepsin cleavage sites as well as the pyridoxal 5'phosphate site. Of particular interest was the isolation of the peptide fraction (m/z 2094.02, SEQISTAGTEASGTGNMKF), which corresponded to the pyridoxal 5'-phosphate site of glycogen phosphorylase A. Traditional procedures required for the characterization of pyridoxal phosphates involve the reduction of the imine to the non-hydrolyzable amine prior to its isolation and characterization. The isolation of the sequence containing the pyridoxal phosphorylation site of glycogen phosphorylase A added an "unexpected" additional advantage to the SPE technique, with respect to the identification of pyridoxal phosphate sites. The additional products shown on the MALDI spectra's correspond to partial hydrolysis of the methyl esters to the free carboxylic acid, as well as different pepsin cleavage sites of the same peptide fraction.

EXAMPLE 4

Alternatively, small linkers can be introduced prior to resin binding. Unlike other methods, this approach is applicable to serine, threonine as well as tyrosine residues.

Methylation of the protein mixture under the conditions described in the earlier examples above protects the carboxylic acid moieties of the protein mixtures. Treatment of the protected protein mixture or digest with the α-diazo-thiol linker covalently links the phosphate to the linker which subsequently undergoes a conjugate addition with the pyrrole 2,5 dione substituted resin similar to the reported procedures (Scheme below).

The diazo group-substituted organic moiety in this approach is linked to a biotin derivative analogous to the biotin derivatives described by McLachlin, D. T.; Chait, B. T. "Analysis of phosphorylated proteins and peptides by mass spectrometry", *Current Opinion in Chemical Biology* 2001, 5, 591-602).

The enriched sample of phosphorylated substrates from the protein of peptide mixture is hydrolyzed from the separtion medium with 10% NH$_4$OH which results in the hydrolysis of the masked carboxylic acids rendering the unmodified phosphoproteins.

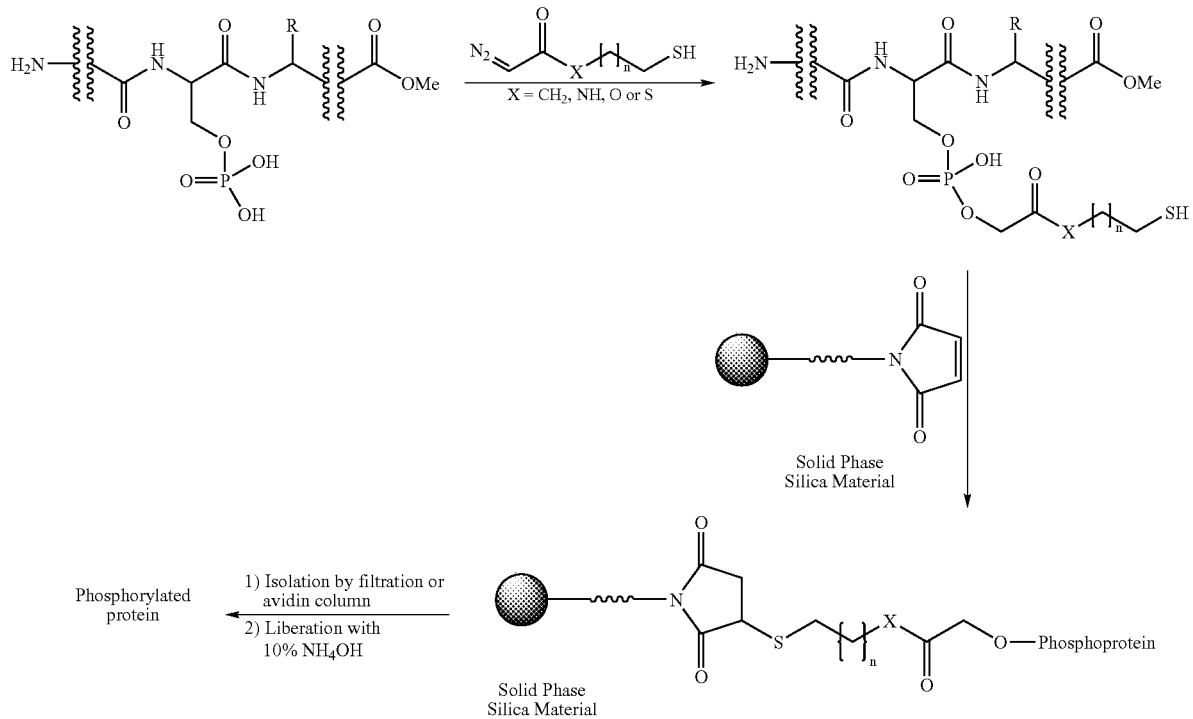

It is intended that the foregoing description be only illustrative of the present invention and that the present invention be limited only by the hereinafter appended claims.

We claim:

1. A method for the separation of a phosphorylated peptide from a complex protein mixture which comprises:
    (a) providing a cell extract comprising a complex protein mixture derived from cell lysis;
    (b) digesting the protein mixture in the cell extract to provide a peptide mixture comprising one or more of the phosphorylated peptide;
    (c) drying the peptide mixture;
    (d) protecting any carboxylate groups in the peptide mixture of step (c) by reaction with an esterification agent or an amination agent or a thiolating agent;
    (e) reacting the mixture of step (d) with a diazo group—substituted organic moiety linked to a separation medium to bind a phosphate group of the phosphorylated peptide to the organic moiety in place of the diazo group;
    (f) separating the phosphorylated peptide bound to the separation medium from the mixture; and
    (g) releasing the bound phosphorylated peptide from the separation medium.

2. A method for the compositional analysis of a phosphorylated peptide from a complex protein isolate mixture which comprises:
    (a) providing a cell extract comprising a complex protein mixture derived from cell lysis;
    (b) digesting the protein mixture in the cell extract to provide a peptide mixture comprising one or more of the phosphorylated peptide;
    (c) drying the peptide mixture;
    (d) protecting any carboxylate groups in the mixture of step (c) by reaction with an esterification agent, an amination agent, thiolating agent or olefins, generating structures of the formulas:

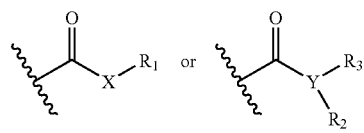

wherein X comprises oxygen or sulfur, Y is nitrogen and R$_1$, R$_2$ and R$_3$ are selected from the group consisting of hydrogen, alkyl, acyl and aryl moieties and mixtures thereof;
    (e) reacting the mixture of step (d) with a diazo group-substituted organic moiety linked to a separation medium to bind a phosphate group of the phosphorylated peptide to the organic moiety in place of the diazo group;
    (f) separating the phosphorylated peptide bound to the separation medium from the mixture;
    (g) releasing the bound phosphorylated peptide from the separation medium; and (h) subjecting the released phosphorylated peptide in step (g) to chemical and physical analytical analysis to at least in part determine the chemical composition of the phosphorylated peptide.

3. The methods of claims 1 or 2 wherein the peptide is from the protein of living cells.

4. The method of claim 1 wherein the carboxylate groups of the peptide are protected from reaction with the diazo groups of the separation medium by reaction methods selected from the group consisting of:
(a) esterification by an esterifying agent selected from the group consisting of alkyl alcohols, aryl alcohols, alkyl halide, aryl halide, alkyl triflate, aryl triflate, and mixtures thereof;
(b) amination by an amidating agent selected from the group comprising an alkyl amine or aryl amine; and
(c) esterification by isobutylene catalyzed by a mineral acid.

5. The methods of claims 1 or 2 wherein the protection of the carboxylate groups of the peptide is carried out in an acidic anhydrous alcohol solution formed by the reaction of an acid chloride or anhydride with alcohols or by protection of the carboxylate groups with isobutylene catalyzed by a mineral acid.

6. The methods of claims 1 or 2 wherein the diazo group substituted organic moiety linked to the separation medium used to bind the phosphate group of the phosphorylated peptide to the separation medium in place of the diazo group has the general formula:

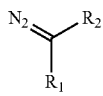

and wherein $R_1$ and $R_2$ are selected from the group comprising of hydrogen, a carbonyl group, an ester, an amide, an aryl group, an alkyl group, an acyl group, an aryl group, an arylalkyl group, a heteroaryl group, a homocyclic ring containing 5-14 carbon atom members, a heterocyclic ring containing 4-12 ring members, organo halides, alkoxides, organo sulfoxides, organo sulfonates, organo phosphonates, and combinations thereof, wherein at least one of $R_1$ or $R_2$ is not hydrogen.

7. The methods of claims 1 or 2 wherein the diazo group used to bind a phosphate group of the phosphorylated peptide to the separation medium in place of the diazo group has the general formula:

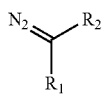

and wherein $R_1$ is hydrogen and $R_2$ is a resonance stabilizing organic moiety.

8. The methods of claims 1 or 2 wherein the diazo group of the separation medium is an α-diazo group prepared by diazotization of an amine functionality.

9. The methods of claims 1 or 2 wherein the diazo group of the separation medium is an α-diazo group prepared by reaction of a diazoalkane with a

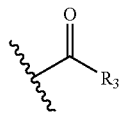

group bound to the separation medium wherein $R_3$ is selected from the group consisting of an amide, a halide, an alkoxide, a thiol, an amine, amide, trichloromethyl, trifluoromethyl, acid, succinamide, cyano, azide, sulfonate, phosphate, sulfite or derivatives thereof.

10. The methods of claims 1 or 2 wherein the diazo group is linked to the separation medium through a linker group consisting of aryl groups (Wang-type linkers), polyethylene glycol (PEG), bis 2-acrylamide based PEG co-polymers (PEGA), Rink amides and derivatives and combinations thereof.

11. The methods of claims 1 or 2 wherein the separation medium is selected from the group consisting of: a resin; a porous resin; a polymer; a thermomorphic polymer; a metal oxide; a metal hydroxide; a mesoporous metal oxide; a mesoporous metal hydroxide; a metal; a layered silicate clay, a layered metal phosphate; a layered metal phosphonate; and combinations thereof.

12. The methods of claims 1 or 2 wherein the separation medium is in thin-film, powdered, bead, gel, foam, sponge, fibrous or liquid form.

13. The methods of claims 1 or 2 wherein the bound phosphorylated peptide is released from the separation medium by a chemical reaction, a thermal reaction, a photochemical reaction, or combinations thereof.

14. The methods of claims 1 or 2 wherein the bound phosphorylated peptide is released from the separation medium through chemical reaction with an acid or a base.

15. The methods of claims 1 or 2 wherein the bound phosphorylated peptide is released from the separation medium by reaction with an acid selected from the group consisting of mineral acids, carboxylic acids, and halogenated carboxylic acids.

16. The method of claim 14 wherein the acid is selected from the group consisting of hydrochloric acid, sulfuric acid, phosphoric acid, acetic acid and trifluoroacetic acid.

17. The methods of claims 1 or 2 wherein the bound phosphorylated peptide is released from the separation medium by reaction with a base selected from the group consisting of sodium hydroxide, ammonium hydroxide, and buffers at a pH value >7.

18. The methods of claims 1 or 2 wherein the bound phosphorylated peptide is released from the separation medium by physical methods selected from the group consisting of ablation and sublimation.

19. The methods of claims 1 or 2 wherein the bound phosphorylated peptide is released from the separation medium by photolytical means by treatment of the separation medium with different wavelengths of light.

20. The methods of claims 1 or 2 wherein the bound phosphorylated peptide is released from the separation medium by enzymatic reaction using enzymes selected from the group comprising esterases, phosphatase, lipases or proteases.

21. The method of claims 1 or 2 wherein the diazo group is linked to the separation medium through a linker group consisting of a chemically, physically or photolytically labile linker.

22. The method of claim 1 wherein the peptide mixture in step (b) is purified to remove unwanted proteins or peptides.

23. A method for the separation of phosphorylated peptide from a complex protein isolate mixture which comprises:
(a) providing a cell extract comprising a complex protein mixture derived from cell lysis;
(b) digesting the protein mixture in the cell extract to provide a peptide mixture comprising one or more of the phosphorylated peptide;
(c) drying the peptide mixture;
(d) protecting any carboxylate groups in the mixture of step (c) by reaction with an esterification agent, an amination agent, a thiolating agent or an olefin to form structures of the formulas:

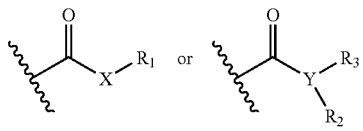

wherein X comprises oxygen or sulfur, Y is nitrogen and $R_1$, $R_2$ and $R_3$ are selected from the group consisting of hydrogen, an alkyl, acyl or aryl moiety and mixtures thereof;
(e) reacting the mixture of step (d) with a diazo group-substituted organic moiety linked to a separation medium to bind a phosphate group of the phosphorylated peptide to the organic moiety in place of the diazo group;
(f) separating the phosphorylated peptide bound to the separation medium from the mixture; and
(g) releasing the bound phosphorylated peptide from the separation medium.

24. A method for the compositional analysis of phosphorylated peptides from a complex protein mixture which comprises:
(a) providing a cell extract comprising a complex protein mixture derived from cell lysis;
(b) digesting the protein mixture in the cell extract to provide a peptide mixture comprising one or more of the phosphorylated peptide;
(c) drying the peptide mixture;
(d) protecting any carboxylate groups in the peptide mixture of step (c) by reaction with an esterification agent, an amination agent, a thiolating agent or an olefin to form structures of the formulas:

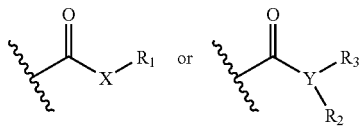

wherein X comprises oxygen or sulfur, Y is nitrogen and $R_1$, $R_2$ and $R_3$ are selected from the group consisting of a hydrogen, an alkyl, acyl or aryl moiety and mixtures thereof;
(e) reacting the mixture of step (d) with a diazo group-substituted organic moiety linked to a separation medium to bind a phosphate group of the phosphorylated peptide mixture to the organic moiety in place of the diazo group;
(f) separating the phosphorylated peptides bound to the separation medium from the mixture;
(g) releasing the bound phosphorylated peptides from the separation medium; and (h) subjecting the released phosphorylated peptides in step (f) to chemical and physical analytical methods to determine the composition of the phosphorylated peptide.

25. A method for the compositional analysis of a phosphorylated peptide from a complex protein mixture by comparison with a reference standard which comprises:
(a) providing a cell extract comprising a complex protein mixture derived from cell lysis;
(b) digesting the protein mixture in the cell extract to provide a peptide mixture comprising one or more of the phosphorylated peptide;
(c) drying the peptide mixture;
(d) protecting any carboxylate groups in the peptide mixture of step (c) by reaction with an esterification agent, an amination agent, a thiolating agent or an olefin to form structures of the formulas:

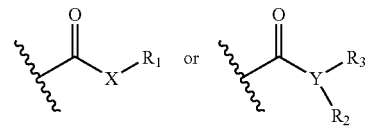

wherein X comprises oxygen or sulfur, Y is nitrogen and $R_1$, $R_2$ and $R_3$ are selected from the group consisting of hydrogen, an alkyl, acyl or aryl moiety and mixtures thereof;
(e) reacting the mixture of step (d) with a diazo group-substituted organic moiety linked to a separation medium to bind a phosphate group of the phosphorylated peptide to the organic moiety in place of the diazo group;
(f) separating the phosphorylated peptides bound to the separation medium from the mixture;
(g) releasing the bound phosphorylated proteins or phosphorylated peptides from the separation medium; and
(h) determining the presence or absence of the separated phosphorylated peptide by comparison with the reference standard.

26. A method for the separation of phosphorylated peptide from a complex protein mixture which comprises:
(a) providing a cell extract comprising a complex protein mixture derived from cell lysis;
(b) digesting the protein mixture in the cell extract to provide a peptide mixture comprising one or more of the phosphorylated peptide;
(c) drying the peptide mixture;
(d) protecting any carboxylate groups in the mixture of step (c) by reaction with an esterification agent, an amination agent, a thiolating agent or an olefin to form structures of the formulas:

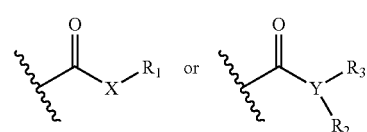

wherein X comprises oxygen or sulfur, Y is nitrogen and $R_1$, $R_2$ and $R_3$ are selected from the group consisting of hydrogen, an alkyl, acyl or aryl moiety and mixtures thereof;
(e) reacting the mixture of step (c) with a diazo group-substituted organic moiety to bind a phosphate group of the phosphorylated peptide to the organic moiety in place of the diazo group;

(f) linking the functionalized phosphorylated peptide of step (e) to a separation medium;
(g) separating the separation medium from the mixture; and
(h) releasing the bound phosphorylated peptide from the separation medium.

27. A method for the compositional analysis of a phosphorylated peptide from a complex protein mixture which comprises:
(a) providing a cell extract comprising a complex protein mixture derived from cell lysis;
(b) digesting the protein mixture in the cell extract to provide a peptide mixture comprising one or more of the phosphorylated peptide;
(c) drying the peptide mixture;
(d) protecting any carboxylate groups in the mixture of step (c) by reaction with an esterification agent, an amination agent, a thiolating agent or an olefin to form structures of the formulas:

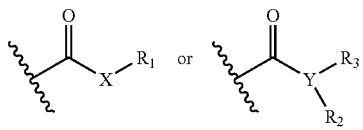

wherein x comprises oxygen or sulfur, Y is nitrogen and $R_1$, $R_2$ and $R_3$ are selected from the group consisting of hydrogen, an alkyl, acyl or aryl moiety and mixtures thereof;
(e) reacting the mixture of step (d) with a diazo group-substituted organic moiety to bind a phosphate group of the phosphorylated peptide to the organic moiety in place of the diazo group;
(f) linking the functionalized phosphorylated proteins or phosphorylated peptide of step (e) to a separation medium;
(g) separating the separation medium from the mixture;
(h) releasing the bound phosphorylated peptide from the separation medium; and
(i) subjecting the released phosphorylated peptide in step (h) to chemical and physical analytical methods to determine the composition of the phosphorylated peptide.

28. The methods of any one of claims 23, 24, 25, 26, and 27 wherein the carboxylate groups of the protein or peptide are protected from reaction with the diazo groups by reaction methods selected from the group comprising:
(a) esterification by an esterifying agent selected from the group comprising alkyl alcohols, aryl alcohols, alkyl halide, aryl halide, alkyl triflate, aryl triflate, and mixtures thereof;
(b) amination by an amidating agent selected from the group comprising an alkyl amine or aryl amine; and
(c) esterification by isobutylene catalyzed by a mineral acid.

29. The methods of any one of claims 23, 24, 25, 26, or 27 wherein the protection of the carboxylate groups of the phosphorylated peptides is carried out in an acidic anhydrous alcohol solution formed by the reaction of an acid chloride or anhydride with alcohols or by protection of the carboxylate groups with isobutylene catalyzed by a mineral acid.

30. The methods of any one of claims 23, 24, 25, 26, or 27 wherein the diazo group used to bind a phosphate group of the phosphorylated protein or peptide with the loss of the $N_2$ has the general formulas:

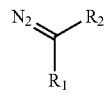

and wherein $R_1$ and $R_2$ are selected from the group comprising of hydrogen, a carbonyl group, an ester, an amide, an aryl group, an alkyl group, an acyl group, an arylalkyl group, a heteroaryl group, a homocyclic ring containing 5-14 carbon atom members, a heterocyclic ring containing 4-12 ring members, organo halides, alkoxides, organo sulfoxides, organo sulfonates, organo phosphonates, and combinations thereof, wherein at least one of $R_1$ or $R_2$ is not hydrogen.

31. The methods of any one of claims 23, 24, 25, 26, or 27 wherein the diazo group used to bind a phosphate group of the phosphorylated peptide to the separation medium with the loss of the $N_2$ has the general formula:

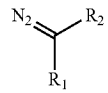

and wherein $R_1$ is hydrogen and $R_2$ is a resonance stabilizing organic moiety.

32. The methods of any one of claims 23, 24, 25, 26, and 27 wherein the diazo group is an α-diazo group prepared by diazotization of an amine functionality.

33. The methods of any one of claims 23, 24, 25, 26, or 27 wherein the diazo group of the separation medium is an α-diazo group prepared by reaction of a diazoalkane with a

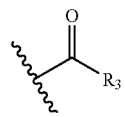

group bound to the separation medium wherein $R_3$ is selected from the group comprising an amide, a halide, an alkoxide, a thiol, an amine, amide, trichloromethyl, trifluoromethyl, acid, succinamide, cyano, azide, sulfonate, phosphite sulfite or derivatives thereof.

34. The methods of any one of claims 23, 24, 25, 26, and 27 wherein the diazo group is linked to the separation medium through a linker group comprising alkyl groups, alkylaryl groups (Wang-type linkers), polyethylene glycol (PEG), bis 2-acrylamide based PEG co-polymers (PEGA), Rink amides and derivatives and combinations thereof.

35. The methods of any one of claims 23, 24, 25, 26, or 27 wherein the separation medium is selected from the group comprising: a resin; a porous resin; a polymer; a thermomorphic polymer; a metal oxide; a metal hydroxide; a mesoporous metal oxide; a mesoporous metal hydroxide; a metal; a layered silicate clay, a layered metal phosphate; a layered metal phosphonate; and combinations thereof.

36. The methods of any one of claims 23, 24, 25, 26, or 27 wherein the separation medium is in thin-film, powdered, bead, gel, foam, sponge, fibrous or liquid form.

37. The methods of any one of claims 23, 24, 25, 26, or 27 wherein the bound phosphorylated peptide is released from the separation medium by methods comprising chemical reaction, thermal reaction, photochemical reaction, and combinations thereof.

38. The methods of any one of claims 23, 24, 25, 26 or 27 wherein the bound phosphorylated peptide is released from the separation medium through chemical reaction with an acid or a base.

39. The methods of any one of claims 23, 24, 25, 26, or 27 wherein the bound phosphorylated peptide is released from the separation medium by reaction with an acid selected from the group comprising mineral acids, carboxylic acids, and halogenated carboxylic acids.

40. The methods according to claim 39 wherein the acid is selected from the group consisting of hydrochloric acid, sulfuric acid, phosphoric acid, acetic acid and trifluoroacetic acid.

41. The methods of any one of claims 23, 24, 25, 26 or 27 wherein the bound phosphorylated peptide is released from the separation medium by reaction with a base selected from the group comprising sodium hydroxide, ammonium hydroxide, and buffers at a pH value >7.

42. The methods of any one of claims 23, 24, 25, 26 or 27 wherein the bound phosphorylated peptide is released from the separation medium by physical methods selected from the group comprising ablation and sublimation.

43. The methods of any one of claims 23, 24, 25, 26 or 27 wherein the bound phosphorylated peptide is released from the separation medium by photolytical means through irradiation of the separation medium with light of different wavelengths.

44. The method of any one of claims 23, 24, 25, 26 or 27 wherein the diazo group is bound to the separation medium through a linker group that is chemically, thermally or photolytically labile.

* * * * *